(12) United States Patent
Epple et al.

(10) Patent No.: US 8,394,841 B2
(45) Date of Patent: Mar. 12, 2013

(54) COMPOUNDS AND METHODS FOR MODULATING G PROTEIN-COUPLED RECEPTORS

(75) Inventors: Robert Epple, San Diego, CA (US); Mihai Azimioara, San Diego, CA (US); Christopher Cow, San Diego, CA (US); Ross Russo, Encinitas, CA (US); Victor Nikulin, San Diego, CA (US); Gerald Lelais, San Diego, CA (US)

(73) Assignee: IRM LLC, Hamilton (BM)

( * ) Notice: Subject to any disclaimer, the term of this patent is extended or adjusted under 35 U.S.C. 154(b) by 300 days.

(21) Appl. No.: 12/527,849

(22) PCT Filed: Jan. 8, 2008

(86) PCT No.: PCT/US2008/050507
§ 371 (c)(1),
(2), (4) Date: Oct. 14, 2009

(87) PCT Pub. No.: WO2008/103501
PCT Pub. Date: Aug. 28, 2008

(65) Prior Publication Data
US 2010/0035944 A1    Feb. 11, 2010

Related U.S. Application Data

(60) Provisional application No. 60/891,178, filed on Feb. 22, 2007.

(51) Int. Cl.
*A61K 31/426*   (2006.01)
*A61K 31/421*   (2006.01)
*C07D 277/20*   (2006.01)
*C07D 263/30*   (2006.01)

(52) U.S. Cl. ........ 514/365; 435/375; 514/374; 548/202; 548/235

(58) Field of Classification Search .................. None
See application file for complete search history.

(56) References Cited

U.S. PATENT DOCUMENTS

| | | | |
|---|---|---|---|
| 6,723,740 B2 * | 4/2004 | Chao et al. | 514/365 |
| 2006/0004012 A1 * | 1/2006 | Akerman et al. | 514/249 |

FOREIGN PATENT DOCUMENTS

| | | |
|---|---|---|
| DE | 2701854 | 7/1977 |
| EP | 0629624 A1 | 12/1994 |
| EP | 0786457 A1 | 7/1997 |
| EP | 1067109 | 1/2001 |
| EP | 1630152 | 3/2006 |
| WO | 2005086661 A2 | 9/2005 |
| WO | 2005116000 A1 | 12/2005 |
| WO | 2005116016 A1 | 12/2005 |
| WO | WO 2005/116000 * | 12/2005 |
| WO | WO2005/116000 * | 12/2005 |
| WO | 2007056366 A2 | 5/2007 |
| WO | WO 2007/056366 A * | 5/2007 |

OTHER PUBLICATIONS

Musser et al., "N-[(Arylmethoxy)phenyl]Carboxylic Acids, Hydroxamic Acids, Tetrazoles, and Sulfonyl Carboxamides. Potent Orally Active Leukotriene D4 Antagonists of Novel Structure," J. Med. Chem. 33: 240-245 (1990).

Meanwell et al., "Nonprostanoid Prostacyclin Mimetics. 2. 2,4-Diphenyloxazole Derivaties," J. Med. Chem. 35: 3483-3497 (1992).

* cited by examiner

*Primary Examiner* — Dennis Heyer
(74) *Attorney, Agent, or Firm* — Emily Tongco Wu; Genomics Institute of the Novartis Research Foundation

(57) ABSTRACT

The invention provides compounds and pharmaceutical compositions thereof, which are useful for modulating G protein-coupled receptor 120 (GPR120), and methods for using such compounds to treat, ameliorate or prevent a condition associated with abnormal or deregulated GPR120.

6 Claims, No Drawings

COMPOUNDS AND METHODS FOR MODULATING G PROTEIN-COUPLED RECEPTORS

CROSS-REFERENCE TO RELATED APPLICATIONS

This application is a 371 U.S. national phase application of international application number PCT/US2008/050507 filed 8 Jan. 2008, which application claims priority to U.S. provisional patent application No. 60/891,178, filed 22 Feb. 2007. The full disclosure of these applications is incorporated herein by reference in its entirety and for all purposes.

TECHNICAL FIELD

The present invention generally relates to G protein-coupled receptors.

BACKGROUND ART

G-protein coupled receptors (GPCRs) constitute a major class of proteins responsible for transducing a signal within a cell. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

GPCR genes and gene-products are potential causative agents of disease (Spiegel et al., J. Clin. Invest. 92:1119 1125 (1993)). For example, specific defects in the rhodopsin gene and the V2 vasopressin receptor gene have been shown to cause various forms of retinitis pigmentosum (Nathans et al., Annu. Rev. Genet. 26:403 424 (1992)), and nephrogenic diabetes insipidus (Holtzman et al., Hum. Mol. Genet. 2:1201 1204 (1993)). These receptors are important to both the central nervous system and peripheral physiological processes.

G protein coupled receptor 120 (GPR120) is an orphan G protein-coupled receptor that is abundantly expressed in intestine, and functions as a receptor for unsaturated long-chain free fatty acids (FFAs). (Hirasawa et al., Nature Medicine 11:90-94 (2005)). Stimulation of GPR120 by FFAs has been reported to promote the secretion of glucagon-like peptide-1 (GLP-1) and increase circulating insulin, and to activate the extracellular signal-regulated kinase (ERK) cascade. (Katsuma et al., J. Biol. Chem. 280:19507-19515 (2005)). Peripherally, GLP-1 affects gut motility, and inhibits gastric acid and glucagon secretion. In the central nervous system, GLP-1 induces satiety, leading to reduced weight gain. In the pancreas, GLP-1 induces expansion of insulin-secreting β-cell mass, in addition to the augmentation of glucose-stimulated insulin secretion. (MacDonald et al., Diabetes 51:Supp. 3 S434-S442 (2002)).

Given the significance of GLP-1 as a potent insulinotropic incretin and in appetite and feeding control, GPR120 is a promising target for the treatment of diabetes, obesity and other eating disorders. Because of the importance of GPCRs as targets for drug action and development, there remains a need for the development of agents which modulate GPCR function.

DISCLOSURE OF THE INVENTION

The invention provides compounds, pharmaceutical compositions and methods of using such compounds for modulating G protein-coupled receptors, more particularly GPR120.

In one aspect, the present invention provides compounds comprising Formula (1):

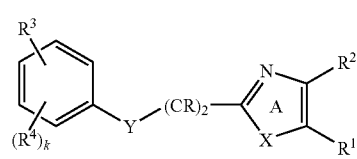

(1)

or pharmaceutically acceptable salts, hydrates, solvates and prodrugs thereof, wherein:

X is O or S;
Y is NR, O or S;
one of $R^1$ or $R^2$ is H or $C_{1-6}$ alkyl, and the other of $R^1$ or $R^2$ is phenyl; said phenyl is optionally substituted with halo, halogenated $C_{1-6}$ alkyl, $C_{2-6}$ alkenyl, $C_{3-6}$ alkynyl, $C_{3-7}$ cycloalkyl, an optionally halogenated $C_{1-6}$ alkoxy, or $OR^5$; or
$R^1$ and $R^2$ together with Ring A may form

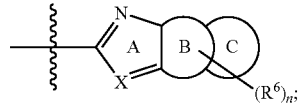

$R^3$ is —O—$(CR^7{}_2)_m$—$CO_2$—R or —$(CR^7{}_2)_m$—$CO_2$—R;
$R^4$ is $C_{1-6}$ alkyl, $C_{2-6}$ alkenyl, $C_{3-6}$ alkynyl, halo, or $C_{1-6}$ alkoxy; or
$R^3$ and $R^4$ or two adjacent $R^4$ together with the carbon atoms to which they are attached to may form a 4-7 membered saturated or unsaturated carbocyclic ring or heterocyclic ring containing N, O or S; wherein said carbocyclic ring or heterocyclic ring is substituted with —O—$(CR^7{}_2)_m$—$CO_2$—R or —$(CR^7{}_2)_m$—$CO_2$—R;
$R^5$ is a $C_{3-7}$ cycloalkyl, or a 5-7 membered aryl, heteroaryl or heterocyclic ring containing N, O or S, each of which is optionally substituted;
$R^6$ is a substituent at any position in Ring B or Ring C, and is halo, an optionally halogenated $C_{1-6}$ alkyl, $C_{2-6}$ alkenyl, $C_{3-6}$ alkynyl, an optionally halogenated $C_{1-6}$ alkoxy, or $OR^5$;
each $R^7$ is H, $C_{1-6}$ alkyl, $C_{2-6}$ alkenylene or OR;
each R is H or $C_{1-6}$ alkyl;
Ring B is a 4-7 membered saturated or unsaturated carbocyclic ring or heterocyclic ring containing N, O or S;
Ring C is aryl;
k is 0-4; and
m and n are independently 0-6.

In the above Formula (1), $R^1$ and $R^2$ together may form

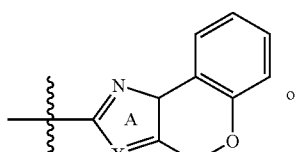

or

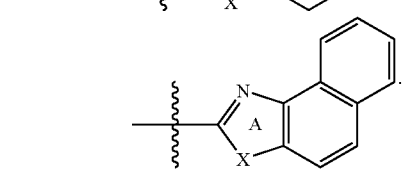

In the above Formula (1), n may be 0.

In one embodiment, the invention provides compounds comprising Formula (2):

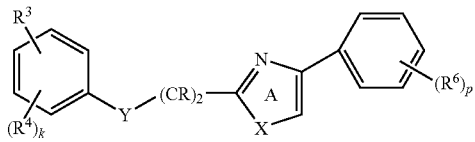

wherein p is 0-5;
$R^6$ is halo, an optionally halogenated $C_{1-6}$ alkyl, $C_{2-6}$ alkenyl, $C_{3-6}$ alkynyl, an optionally halogenated $C_{1-6}$ alkoxy, or $OR^5$; and
X, Y, R, $R^3$, $R^4$, and k are as defined in Formula (1).

In the above Formula (2), p may be 1-2 and $R^6$ is halo. In some examples, $R^6$ is chloro.

In the above Formula (1) and (2), k may be 1 and $R^4$ is $C_{1-6}$ alkyl or $C_{1-6}$ alkoxy.

In the above Formula (1) and (2), m may be 0-3.

In the above Formula (1) and (2), $R^3$ and $R^4$ or two adjacent $R^4$ together with the carbon atoms to which they are attached to may form

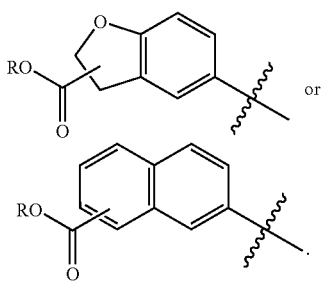

In another aspect, the present invention provides pharmaceutical compositions comprising a compound of Formula (1) or (2), and a pharmaceutically acceptable excipient.

In yet another aspect, the invention provides methods for modulating G protein-coupled receptor 120 (GPR120), comprising administering to a cell or tissue system or to a mammalian subject, a therapeutically effective amount of a compound comprising Formula (1) or (2), or pharmaceutically acceptable salts or pharmaceutical compositions thereof, and optionally in combination with a second therapeutic agent, thereby modulating said GPR120. In particular embodiments, compounds of the invention are GPR120 agonists.

The invention also provides methods for preventing, ameliorating or treating a condition mediated by G protein-coupled receptor 120 (GPR120), comprising administering to a cell or tissue system or to a mammalian subject, an effective amount of a compound comprising Formula (1) or (2), or pharmaceutically acceptable salts or pharmaceutical compositions thereof, and optionally with a second therapeutic agent, thereby treating said condition.

Furthermore, the present invention provides the use of a compound of Formula (1) or (2), for treating a condition mediated by G protein-coupled receptor 120 (GPR120). The present invention also provides the use of a compound of Formula (1) or (2) in the manufacture of a medicament for treating a condition mediated by GPR120.

Examples of conditions which may be ameliorated or treated using the compounds of the invention include but are not limited to diabetes such as diabetes mellitus, dyslipidemia such as hyperlipidemia, obesity or anorexia.

DEFINITIONS

"Alkyl" refers to a moiety and as a structural element of other groups, for example halo-substituted-alkyl and alkoxy, and may be straight-chained or branched. An optionally substituted alkyl, alkenyl or alkynyl as used herein may be optionally halogenated (e.g., $CF_3$), or may have one or more carbons that is substituted or replaced with a heteroatom, such as NR, O or S (e.g., —$OCH_2CH_2O$—, alkylthiols, thioalkoxy, alkylamines, etc).

"Aryl" refers to a monocyclic or fused bicyclic aromatic ring containing carbon atoms. For example, aryl may be phenyl or naphthyl. "Arylene" means a divalent radical derived from an aryl group.

"Heteroaryl" as used herein is as defined for aryl above, where one or more of the ring members is a heteroatom. Examples of heteroaryls include but are not limited to pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

A "carbocyclic ring" as used herein refers to a saturated or partially unsaturated, monocyclic, fused bicyclic or bridged polycyclic ring containing carbon atoms, which may optionally be substituted, for example, with =O. Examples of carbocyclic rings include but are not limited to cyclopropyl, cyclobutyl, cyclopentyl, cyclohexyl, cyclopropylene, cyclohexanone, etc.

A "heterocyclic ring" as used herein is as defined for a carbocyclic ring above, wherein one or more ring carbons is a heteroatom. For example, a heterocyclic ring may contain N, O, S, —N=, —S—, —S(O), —S(O)$_2$—, or —NR— wherein R may be hydrogen, $C_{1-4}$alkyl or a protecting group. Examples of heterocyclic rings include but are not limited to morpholino, pyrrolidinyl, pyrrolidinyl-2-one, piperazinyl, piperidinyl, piperidinylone, 1,4-dioxa-8-aza-spiro[4.5]dec-8-yl, etc.

Unless otherwise indicated, when a substituent is deemed to be "optionally substituted," it is meant that the substituent is a group that may be substituted with one or more group(s) individually and independently selected from, for example, an optionally halogenated alkyl, alkenyl, alkynyl, alkoxy, alkylamine, alkylthio, alkynyl, amide, amino, including mono- and di-substituted amino groups, aryl, aryloxy, arylthio, carbonyl, carbocyclic, cyano, cycloalkyl, halogen, heteroalkyl, heteroalkenyl, heteroalkynyl, heteroaryl, heterocyclic, hydroxy, isocyanato, isothiocyanato, mercapto, nitro, O-carbamyl, N-carbamyl, O-thiocarbamyl, N-thiocarbamyl, C-amido, N-amido, S-sulfonamido, N-sulfonamido, C-carboxy, O-carboxy, perhaloalkyl, perfluoroalkyl, silyl, sulfonyl, thiocarbonyl, thiocyanato, trihalomethanesulfonyl, and the protected compounds thereof. The protecting groups that may form the protected compounds of the above substituents are known to those of skill in the art and may be found in references such as Greene and Wuts, Protective Groups in Organic Synthesis, 3$^{rd}$ Ed., John Wiley & Sons, New York, N.Y., 1999, and Kocienski, Protective Groups, Thieme Verlag, New York, N.Y., 1994, which are incorporated herein by reference in their entirety.

The terms "co-administration" or "combined administration" or the like as used herein are meant to encompass administration of the selected therapeutic agents to a single patient, and are intended to include treatment regimens in which the agents are not necessarily administered by the same route of administration or at the same time.

The term "pharmaceutical combination" as used herein refers to a product obtained from mixing or combining active ingredients, and includes both fixed and non-fixed combinations of the active ingredients. The term "fixed combination" means that the active ingredients, e.g. a compound of Formula (1) and a co-agent, are both administered to a patient simultaneously in the form of a single entity or dosage. The term "non-fixed combination" means that the active ingredients, e.g. a compound of Formula (1) and a co-agent, are both administered to a patient as separate entities either simultaneously, concurrently or sequentially with no specific time limits, wherein such administration provides therapeutically effective levels of the active ingredients in the body of the patient. The latter also applies to cocktail therapy, e.g. the administration of three or more active ingredients.

The term "therapeutically effective amount" means the amount of the subject compound that will elicit a biological or medical response in a cell, tissue, organ, system, animal or human that is being sought by the researcher, veterinarian, medical doctor or other clinician.

The term "administration" and or "administering" of the subject compound should be understood to mean as providing a compound of the invention including a pro-drug of a compound of the invention to the individual in need of treatment.

As used herein, the terms "treat", "treating" and "treatment" refer to a method of alleviating or abating a disease and/or its attendant symptoms.

MODES OF CARRYING OUT THE INVENTION

The invention provides compounds, pharmaceutical compositions and methods of using such compounds for modulating G protein-coupled receptors, more particularly GPR120.

In one aspect, the present invention provides compounds comprising Formula (1):

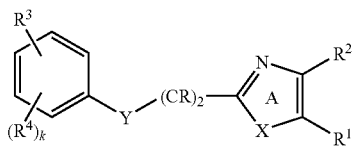

or pharmaceutically acceptable salts, hydrates, solvates and prodrugs thereof, wherein:

X is O or S;
Y is NR, O or S;
one of $R^1$ or $R^2$ is H or $C_{1-6}$ alkyl, and the other of $R^1$ or $R^2$ is phenyl; said phenyl is optionally substituted with halo, halogenated $C_{1-6}$ alkyl, $C_{2-6}$ alkenyl, $C_{3-6}$ alkynyl, $C_{3-7}$ cycloalkyl, an optionally halogenated $C_{1-6}$ alkoxy, or $OR^5$; or
$R^1$ and $R^2$ together with Ring A may form

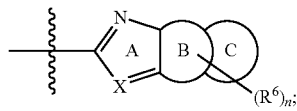

$R^3$ is $—O—(CR^7_2)_m—CO_2—R$ or $—(CR^7_2)_m—CO_2—R$;
$R^4$ is $C_{1-6}$ alkyl, $C_{2-6}$ alkenyl, $C_{3-6}$ alkynyl, halo, or $C_{1-6}$ alkoxy; or
$R^3$ and $R^4$ or two adjacent $R^4$ together with the carbon atoms to which they are attached to may form a 4-7 membered saturated or unsaturated carbocyclic ring or heterocyclic ring containing N, O or S; wherein said carbocyclic ring or heterocyclic ring is substituted with $—O—(CR^7_2)_m—CO_2—R$ or $—(CR^7_2)_m—CO_2—R$;

$R^5$ is a $C_{3-7}$ cycloalkyl, or a 5-7 membered aryl, heteroaryl or heterocyclic ring containing N, O or S, each of which is optionally substituted;

$R^6$ is a substituent at any position in Ring B or Ring C, and is halo, an optionally halogenated $C_{1-6}$ alkyl, $C_{2-6}$ alkenyl, $C_{3-6}$ alkynyl, an optionally halogenated $C_{1-6}$ alkoxy, or $OR^5$;
each $R^7$ is H, $C_{1-6}$ alkyl, $C_{2-6}$ alkenylene or OR;
each R is H or $C_{1-6}$ alkyl;
Ring B is a 4-7 membered saturated or unsaturated carbocyclic ring or heterocyclic ring containing N, O or S;
Ring C is aryl;
k is 0-4; and
m and n are independently 0-6.

In one embodiment, the invention provides compounds comprising Formula (2):

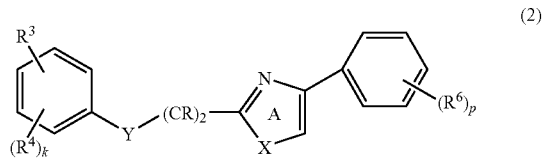

wherein p is 0-5;
$R^6$ is halo, an optionally halogenated $C_{1-6}$ alkyl, $C_{2-6}$ alkenyl, $C_{3-6}$ alkynyl, an optionally halogenated $C_{1-6}$ alkoxy, or $OR^5$; and
X, Y, R, $R^3$, $R^4$, and k are as defined in Formula (1).

In other embodiments, the $R^2$ phenyl group may be substituted with $C_{1-6}$ alkyl, or $R^6$ in Formula (2) may be $C_{1-6}$ alkyl, provided X is O.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include but are not limited to isotopes of hydrogen, carbon, nitrogen and oxygen such as $^2H$, $^3H$, $^{11}C$, $^{13}C$, $^{14}C$, $^{15}N$, $^{17}O$, $^{18}O$, $^{35}S$, $^{18}F$, $^{36}Cl$ and $^{123}I$. Certain isotopic variations of the compounds of the invention and pharmaceutically acceptable salts thereof, for example, those in which a radioactive isotope such as $^3H$ or $^{14}C$ is incorporated, are useful in drug and/or substrate tissue distribution studies. In particular examples, $^3H$ and $^{14}C$ isotopes may be used for their ease of preparation and detectability. In other examples, substitution with isotopes such as $^2H$ may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

The compounds of the invention may be useful for modulating G protein-coupled receptors (GPCRs), particularly GPR120. For example, compounds of the invention may be useful as GPR120 agonists. Compounds of the invention may also be useful for treating conditions mediated by GPR120, including but are not limited to diabetes such as diabetes mellitus, dyslipidemia such as hyperlipidemia, obesity or anorexia.

Pharmacology and Utility

Compounds of the invention may modulate G protein-coupled receptors, and as such, are useful for treating diseases or disorders in which GPCR contribute to the pathology and/or symptomology of the disease. More particularly, the compounds of the invention may be used to prevent, ameliorate or treat a condition mediated by G protein-coupled receptor 120 (GPR120).

Examples of conditions mediated by GPR120 include but are not limited to obesity, diabetes, hyperphagia, endocrine abnormalities, triglyceride storage disease, Bardet-Biedl syndrome, Lawrence-Moon syndrome, Prader-Labhart-Willi syndrome, anorexia, and cachexia. In particular examples, obesity is defined as a body mass index (BMI) of 30 kg/m or more (National Institute of Health, Clinical Guidelines on the Identification, Evaluation, and Treatment of Overweight and Obesity in Adults (1998)). However, the compounds of the invention may be used to prevent, ameliorate or treat a condition characterized by a body mass index (BMI) of 25 kg/m or more, 26 kg/m or more, 27 kg/m or more, 28 kg/m or more, 29 kg/m or more, 29.5 kg/m or more, or 29.9 kg/m or more, all of which are typically referred to as overweight (National Institute of Health, Clinical Guidelines on the Identification, Evaluation, and Treatment of Overweight and Obesity in Adults (1998)).

In some embodiments, the compounds of the invention may be useful as an agent for regulating glycerol production from adipocytes, an agent for regulating blood glycerol, an agent for regulating lipolysis, an insulin resistance regulating agent, a stress regulating agent, an agent for regulating adrenocorticotropic hormone (ACTH) secretion, an agent for regulating growth hormone secretion, and an agent for regulating glucagon-like peptide-1 (GLP-1) secretion.

Compounds of the invention that are GPR120 agonists, or that potentiate the binding affinity of free fatty acids to GPR120, may be useful as an agent for suppressing glycerol production from adipocytes, an agent for lowering blood glycerol, an agent for suppressing lipolysis, an agent for suppressing insulin resistance, a stress regulating agent, an adrenocorticotropic hormone (ACTH) secretion suppressing agent, a growth hormone secretion suppressing agent and a glucagon-like peptide-1 (GLP-1) secretion promoting agent. In particular examples, the GPR agonists useful as an adrenocorticotropic hormone (ACTH) secretion suppressing agent may be useful for preventing/treating related diseases, such as ACTH-producing tumor, Cushing's disease, infectious disease, secondary adrenocortical insufficiency, peptic ulcer, diabetes mellitus, mental disorder, cataract, glaucoma, tuberculous disease, hypertension, Cushing's syndrome (e.g., central obesity, edema, hypertension, menstrual disorder, extensive stretch mark, hirsutism, diabetes mellitus, full moon face, osteoporosis, hemorrhagic diathesis, mental disorder (e.g., depression, anxiety), muscular atrophy, loss of muscle strength, hypokalemia, hypercholesterolemia, impaired glucose resistance, leukocytosis), adrenocortical atrophy, etc.

Compounds of the invention that are GPR120 antagonists, or that reduce the binding affinity of free fatty acids to GPR120, may be useful as an agent for promoting glycerol production from adipocytes, an agent for increasing blood glycerol, an agent for promoting lipolysis, an agent for promoting insulin resistance, a stress regulating agent, an agent for promoting adrenocorticotropic hormone (ACTH) secretion, an agent for promoting growth hormone secretion and an agent for suppressing glucagon-like peptide-1 (GLP-1) secretion). In particular examples, the GPR120 antagonists useful as an agent for promoting adrenocorticotropic hormone (ACTH) secretion may be useful for preventing/treating connective tissue diseases (e.g., chronic articular rheumatism, systemic lupus erythematosus, polymyositis, rheumatic fever, scleroderma), kidney diseases (e.g., nephrosis), respiratory diseases (e.g., bronchial asthma, pulmonary tuberculous pleuritis, sarcoidosis, diffuse interstitial pneumonia), alimentary diseases (e.g., ulcerative colitis, cholestatic acute hepatitis, fulminant hepatitis, chronic hepatitis, cirrhosis), neuromuscular diseases (e.g., encephalomyelitis, peripheral neuritis, multiple sclerosis, myasthenia gravis, facial paralysis), blood diseases (e.g., hemolytic anemia, agranulocytosis, purpura, aplastic anemia, leukemia, malignant lymphoma), endocrine-metabolic diseases (e.g., acute or chronic adrenocortical insufficiency, adrenogenital syndrome, malignant exopthalmos due to thyroid gland disease, ACTH isolated deficiency), skin diseases (e.g., urticaria, eczema, dermatitis, herpes zoster, psoriasis, drug allergy) or anaphylactic shock, etc.

Compounds of the invention may also be useful as an agent for preventing/treating, for example, diabetes mellitus, impaired glucose tolerance, ketosis, acidosis, diabetic neuropathy, diabetic nephropathy, diabetic retinopathy, hyperlipemia, arteriosclerosis, angina pectoris, myocardial infarction, sexual dysfunction, obesity, pituitary dysfunctions (e.g., hypopituitarism, pituitary dwarfism, diabetes insipidus, acromegaly, Cushing's disease, hyperprolactinemia, syndrome of inappropriate secretion of anti-diuretic hormone), cancer (e.g., colorectal cancer), deficits in memory and learning, pancreatic exhaustion, hypoglycemia, insulin allergy, lipotoxicity, fatty atrophy, cancerous cachexia, hyperinsulinemia, hyperglycemia, disorder caused by high FFA flux, hypertriglyceridemia, fatty liver, dysfunction of heat production, cholelithiasis, eating disorder, anorexia, secretion disorders of intestinal hormones (e.g., cholecystokinin (CCK), gastric inhibitory peptide (GIP), gastrin, glucagon-like peptide-1 (GLP-1), somatostatin, gastrin-releasing peptide, secretin, vasoactive intestinal peptide, motilin, substance P, neurotensin, galanin, neuropeptide Y, enkephalins, peptide YY, etc.) or circulatory diseases. GPR120 agonists may be particularly useful for preventing/treating diabetes mellitus, hyperlipemia, arteriosclerosis, angina pectoris or myocardial infarction, while GPR120 antagonists may be useful for preventing/treating anorexia and obesity, such as obesity with visceral fat accumulation).

Furthermore, compounds of the invention may be useful as an agent for preventing/treating diseases, for example, arteriosclerosis, arteriosclerotic diseases and their secondary diseases [e.g., acute coronary syndrome such as atherosclerosis, peripheral arterial disease, acute myocardial infarction, unstable angina, etc., ischemic heart diseases such as restenosis after percutaneous transluminal coronary angioplasty (PTCA), myocardial infarction, angina pectoris, etc., arteriosclerosis including angiocalcinosis, etc., intermittent claudication, apoplexy (cerebral infarction, cerebral embolism, brain hemorrhage, etc.), lacunar infarction, cerebrovascular dementia, gangrene, glomerulosclerosis, nephropathy, Tangier disease, etc.], vascular lesions in atherosclerosis and their secondary diseases (e.g., coronary heart disease (CHD), cerebral ischemia, etc.), lipid dysbolism and its secondary diseases, etc.

Administration and Pharmaceutical Compositions

In general, compounds of the invention will be administered in therapeutically effective amounts via any of the usual and acceptable modes known in the art, either singly or in combination with one or more therapeutic agents. The compounds of the invention may be mixed with the other therapeutic agent in a fixed pharmaceutical composition, or may be administered separately, before, simultaneously with or after the other therapeutic agent.

Accordingly, the invention encompasses compounds of the invention, which may be used in combination with other therapeutic substances such as therapeutic agents for treating diabetes, diabetic complications, dyslipidemia and more particularly hyperlipidemia; antihypertensive agents, antiobesity agents, diuretics, chemotreating agents, immunotreating agents, immunomodulators, anti-inflammatory agents, antithrombotic agents, therapeutic agents for osteoporosis, antibacterial agents, antifungal agents, antiprotozoal agents, antibiotics, antitussives and expectorant drugs, sedatives, anesthetics, antiulcer agents, tranquilizers, antipsychotic agents, antitumor agents, muscle relaxants, antiepileptics, antidepressants, antiallergic agents, cardiac stimulants, antiarrhythmic agents, vasodilators, vasoconstrictors, narcotic antagonists, vitamins, vitamin derivatives, antiasthmatic agents, antidementia agents, treating agents for pollakiuria or urinary incontinence, therapeutic agents for dysuria, treating agents for atopic dermatitis, therapeutic agents for allergic rhinitis, vasopressors, endotoxin antagonists or antibodies, signal transduction inhibitors, inflammatory mediator effect suppressants, inflammatory mediator effect suppressing antibodies, anti-inflammatory mediator effect suppressants, anti-inflammatory mediator effect suppressing antibodies and the like.

Therapeutic agents for diabetes include but are not limited to insulin preparations (e.g., animal insulin preparations extracted from pancreas of bovine or pig; human insulin preparations genetically synthesized using *Escherichia coli* or yeast; zinc insulin; protamine zinc insulin; fragment or derivative of insulin (e.g., INS-1, etc.), oral insulin preparation and the like), insulin sensitizers (e.g., pioglitazone or a salt thereof (preferably hydrochloride), troglitazone, rosiglitazone or a salt thereof (preferably maleate), Reglixane (JTT-501), Netoglitazone (MCC-555), YM-440, GI-262570, KRP-297, FK-614, CS-011, (E)-[[[4-[(5-methyl-2-phenyl-4-oxazolyl)methoxy]phenyl]methoxy]imino]benzenebutanoic acid and the like, compounds described in WO 99/58510 (e.g., (E)-4-[4-(5-methyl-2-phenyl-4-oxazolylmethoxy)-benzyloxyimino]-4-phenylbutyric acid), compounds described in WO 01/38325, Tesaglitazar (AZ-242), Ragaglitazar (N,N-622), BMS-298585, ONO-5816, BM-13-1258, LM-4156, MBX-102, LY-519818, MX-6054, LY-510929, Balaglitazone (N,N-2344), T-131 or a salt thereof, THR-0921), -glucosidase inhibitors (e.g., voglibose, acarbose, miglitol, emiglitate, etc.), biguanides (e.g., phenformin, metformin, buformin, etc.), insulin secretagogues [sulfonylurea (e.g., tolbutamide, glibenclamide, gliclazide, chlorpropamide, tolazamide, acetohexamide, glyclopyramide, glimepiride, etc.), repaglinide, senaglinide, mitiglinide or calcium salt hydrate thereof, nateglinide, etc.], GLP-1 receptor agonists [e.g., GLP-1, GLP-1MR agent, N,N-2211, AC-2993 (exendin-4), BIM-51077, Aib(8.35)hGLP-1 (7.37)NH2, CJC-1131, etc.], dipeptidyl peptidase IV inhibitors (e.g., NVP-DPP-278, PT-100, P32/98, P93/01, NVP-DPP-728, LAF237, TS-021, etc.), 3 agonists (e.g., CL-316243, SR-58611-A, UL-TG-307, AJ-9677, AZ40140, etc.), amylin agonists (e.g., pramlintide, etc.), phosphotyrosine phosphatase inhibitors (e.g., vanadic acid, etc.), gluconeogenesis inhibitors (e.g., glycogen phosphorylase inhibitors, glucose-6-phosphatase inhibitors, glucagon antagonists, etc.), SGLT (sodium-glucose cotransporter) inhibitors (e.g., T-1095, etc.), 11-hydroxysteroid dehydrogenase inhibitors (e.g., BVT-3498, etc.), adiponectin or agonists thereof, IKK inhibitors (e.g., AS-2868, etc.), leptin resistance improving drugs, somatostatin receptor agonists (compounds described in WO 01/25228, WO 03/42204, compounds described in WO 98/44921, WO 98/45285, WO 99/22735, etc.), glucokinase activators (e.g., Ro-28-1675) and the like.

Therapeutic agents for treating diabetic complications include but are not limited to aldose reductase inhibitors (e.g., Tolrestat, Epalrestat, Zenarestat, Zopolrestat, Fidarestat (SNK-860), Minalrestat (ARI-509), CT-112, etc.), neurotrophic factors and increasing drugs thereof (e.g., NGF, NT-3, BDNF, neurotrophin production-secretion promoters described in WO 01/14372 (e.g., 4-(4-chlorophenyl)-2-(2-methyl-1-imidazolyl)-5-[3-(2-methylphenoxy)propyl]oxazole, etc.) and the like), protein kinase C (PKC) inhibitors (e.g., LY-333531, etc.), AGE inhibitors (e.g., ALT-945, pimagedine, pyratoxanthine, N-phenacylthiazolium bromide (ALT-766), EXO-226, ALT-711, Pyridorin, Pyridoxamine, etc.), active oxygen scavengers (e.g., thioctic acid, etc.), cerebral vasodilators (e.g., tiapuride, etc.), somatostatin receptor agonist (BIM23190), apoptosis signal regulating kinase-1 (ASK-1) inhibitors and the like.

Therapeutic agents for treating hyperlipidemia include but are not limited to statin compounds which are cholesterol synthesis inhibitors (e.g., pravastatin, simvastatin, lovastatin, atorvastatin, fluvastatin, cerivastatin or a salt thereof (e.g., sodium salt, etc.), etc.), squalene synthase inhibitors (e.g., compounds described in WO 97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl]acetyl]piperidine-4-acetic acid and the like), fibrate compounds (e.g., bezafibrate, clofibrate, simfibrate, clinofibrate, etc.), antioxidants (e.g., lipoic acid, probucol) and the like.

Examples of the antihypertensive agents include but are not limited to angiotensin converting enzyme inhibitors (e.g., captopril, enalapril, delapril, etc.), angiotensin II antagonists (e.g., losartan, candesartan, cilexetil, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid, etc.), calcium antagonists (e.g., manidipine, nifedipine, amlodipine, efonidipine, nicardipine, etc.), clonidine and the like.

Examples of the antiobesity agents include but are not limited to antiobesity agents acting on the central nervous system (e.g., dexfenfluramine, fenfluramine, phentermine, sibutramine, amfepramone, dexamphetamine, mazindol, phenylpropanolamine, clobenzorex; MCH receptor antagonists (e.g., SB-568849; SNAP-7941; compounds encompassed in WO 01/82925 and WO 01/87834, etc.); neuropeptide Y antagonists (e.g., CP-422935, etc.); cannabinoid receptor antagonists (e.g., SR-141716, SR-147778, etc.); ghrelin antagonists; 11-hydroxysteroid dehydrogenase inhibitors (e.g., BVT-3498, etc.) and the like), pancreatic lipase inhibitors (e.g., orlistat, ATL-962, etc.), 3 agonists (e.g., CL-316243, SR-58611-A, UL-TG-307, AJ-9677, AZ40140, etc.), peptide anorexiants (e.g., leptin, CNTF (Ciliary Neurotropic Factor), etc.), cholecystokinin agonists (e.g., lintitript, FPL-15849, etc.), feeding deterrent (e.g., P-57, etc.) and the like.

Examples of the diuretics include but are not limited to xanthine derivatives (e.g., theobromine sodium salicylate, theobromine calcium salicylate, etc.), thiazide preparations (e.g., ethiazide, cyclopenthiazide, trichloromethiazide, hydrochlorothiazide, hydroflumethiazide, benzylhydrochlorothiazide, penflutizide, polythiazide, methyclothiazide, etc.), antialdosterone preparations (e.g., spironolactone, triamterene, etc.), carbonate dehydratase inhibitors (e.g., acetazolamide and the like), chlorobenzenesulfonamide preparations (e.g., chlorthalidone, mefruside, indapamide, etc.), azosemide, isosorbide, ethacrynic acid, piretanide, bumetanide, furosemide and the like.

Examples of the chemotreating agents include but are not limited to alkylating agents (e.g., cyclophosphamide, ifosfamide, etc.), metabolic antagonists (e.g., methotrexate, 5-fluorouracil, etc.), antitumor antibiotics (e.g., mitomycin, adriamycin, etc.), plant-derived antitumor agent (e.g., vincristine, vindesine, Taxol, etc.), cisplatin, carboplatin, etoposide and the like.

Examples of the immunotreating agents include but are not limited to microorganism or bacterial components (e.g., muramyl dipeptide derivative, Picibanil, etc.), polysaccharides having immunity potentiating activity (e.g., lentinan, schizophyllan, krestin, etc.), cytokines obtained by genetic engineering techniques (e.g., interferon, interleukin (IL), etc.), colony stimulating factors (e.g., granulocyte colony stimulating factor, erythropoietin, etc.) and the like, with preference given to interleukins such as IL-1, IL-2, IL-112 and the like.

Examples of the anti-inflammatory agents include but are not limited to non-steroidal anti-inflammatory agents such as aspirin, acetaminophen, indomethacin and the like.

Examples of the antithrombotic agents include but are not limited to heparin (e.g., heparin sodium, heparin calcium, dalteparin sodium, etc.), warfarin (e.g., warfarin potassium, etc.), antithrombin drugs (e.g., aragatroban, etc.), thrombolytic agents (e.g., urokinase, tisokinase, alteplase, nateplase, monteplase, pamiteplase, etc.), platelet aggregation suppressors (e.g., ticlopidine hydrochloride, cilostazol, ethyl icosapentate, beraprost sodium, sarpogrelate hydrochloride, etc.) and the like.

Therapeutic agents for treating osteoporosis include but are not limited to alfacalcidol, calcitriol, elcatonin, calcitonin salmon, estriol, ipriflavone, pamidronate disodium, alendronate sodium hydrate, incadronate disodium and the like.

Examples of the vitamins which may be used in combination with the compounds of the invention include but are not limited to vitamin B1, vitamin B12 and the like, and derivatives thereof.

Examples of the antidementia agents include but are not limited to tacrine, donepezil, rivastigmine, galantamine and the like.

Therapeutic agents for pollakiuria or urinary incontinence include but are not limited to flavoxate hydrochloride, oxybutynin hydrochloride, propiverine hydrochloride and the like.

Therapeutic agents for dysuria include but are not limited to acetylcholine esterase inhibitors (e.g., distigmine) and the like.

Furthermore, therapeutic agents having a cachexia-improving effect in animal models and clinical situations, may be used in combination with the compound of the invention. Examples of such therapeutic agents include but are not limited to cyclooxygenase inhibitors (e.g., indomethacin, etc.) [Cancer Research, Vol. 49, pp. 5935-5939, 1989], progesterone derivatives (e.g., megestrol acetate) [Journal of Clinical Oncology, Vol. 12, pp. 213-225, 1994], glucosteroids (e.g., dexamethasone, etc.), metoclopramide agents, tetrahydrocannabinol agents (publications are all as mentioned above), fat metabolism improving agents (e.g., eicosapentanoic acid, etc.) [British Journal of Cancer, Vol. 68, pp. 314-318, 1993], growth hormones, IGF-1, or antibodies to a cachexia-inducing factor such as TNF-, LIF, IL-6, oncostatin M and the like.

Furthermore, glycosylation inhibitors (e.g., ALT-711, etc.), nerve regeneration promoting drugs (e.g., Y-128, VX853, prosaptide, etc.), antidepressants (e.g., desipramine, amitriptyline, imipramine, etc.), antiepileptics (e.g., lamotrigine, Trileptal, Keppra, Zonegran, Pregabalin, Harkoseride, carbamazepine), antiarrhythmic agents (e.g., mexiletine), acetylcholine receptor ligands (e.g., ABT-594), endothelin receptor antagonists (e.g., ABT-627), monoamine uptake inhibitors (e.g., tramadol), narcotic analgesics (e.g., morphine), GABA receptor agonists (e.g., gabapentin, gabapentin MR preparations), 2 receptor agonists (e.g., clonidine), local analgesics (e.g., capsaicin), antianxiety drugs (e.g., benzodiazepines), phosphodiesterase inhibitors (e.g., sildenafil), dopamine receptor agonists (e.g., apomorphine) and the like may also be used in combination with the compounds of the invention.

A therapeutically effective amount may vary widely depending on the severity of the disease, the age and relative health of the subject, the potency of the compound used and other factors. In general, satisfactory results are indicated to be obtained systemically at daily dosages of from about 0.01 to 2.5 mg/kg per body weight. An indicated daily dosage in the larger mammal, e.g. humans, is in the range from about 0.01 mg/kg per body weight to about 100 mg, conveniently administered, e.g. in divided doses up to four times a day or in retard form. Suitable unit dosage forms for oral administration comprise from ca. 0.01 to 50 mg/kg per body weight. For example, a compound of the invention (as an active ingredient) may be orally administered to a patient with hyperlipidemia in about 0.01 to about 30 mg/kg of body weight per day; in some examples, from about 0.1 to about 20 mg/kg of body weight per day; and in other examples, from about 1 to about 20 mg/kg of body weight per day, which may be given at once or in several portions a day.

Compounds of the invention may be administered as pharmaceutical compositions by any conventional route known in the art, such as those described in EP 1688138, incorporated by reference herein in its entirety. For example, compounds of the invention may be administered enterally, e.g., orally, e.g., in the form of tablets or capsules, or parenterally, e.g., in the form of injectable solutions or suspensions, topically, e.g., in the form of lotions, gels, ointments or creams, or in a nasal or suppository form.

Pharmaceutical compositions comprising a compound of the present invention in free form or in a pharmaceutically acceptable salt form in association with at least one pharmaceutically acceptable carrier or diluent may be manufactured in a conventional manner by mixing, granulating or coating methods. For example, oral compositions may be tablets or gelatin capsules comprising the active ingredient together with a) diluents, e.g., lactose, dextrose, sucrose, mannitol, sorbitol, cellulose and/or glycine; b) lubricants, e.g., silica, talcum, stearic acid, its magnesium or calcium salt and/or polyethyleneglycol; for tablets, together with c) binders, e.g., magnesium aluminum silicate, starch paste, gelatin, tragacanth, methylcellulose, sodium carboxymethylcellulose and or polyvinylpyrrolidone; and if desired, d) disintegrants, e.g., starches, agar, alginic acid or its sodium salt, or effervescent mixtures; and/or e) absorbents, colorants, flavors and sweeteners. Injectable compositions may be aqueous isotonic solutions or suspensions, and suppositories may be prepared from fatty emulsions or suspensions.

The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Suitable formulations for transdermal applications include an effective amount of a compound of the present invention with a carrier.

A carrier may include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound to the skin of the host at a controlled and predetermined rate over a prolonged period of time, and means to secure the device to the skin. Matrix transdermal formulations may also be used. Suitable formulations for topical application, e.g., to the skin and eyes, may be aqueous solutions, ointments, creams or gels well-known in the art. Such may contain solubilizers, stabilizers, tonicity enhancing agents, buffers and preservatives.

The invention also provides kits of a pharmaceutical combinations, comprising a) a first agent comprising a compound of Formula (1) or (2), in free form or in pharmaceutically acceptable salt form, and b) at least one co-therapeutic agent. The kit may further comprise instructions for its administration.

Processes for Making Compounds of the Invention

The compounds of the invention may be prepared, following procedures exemplified in the Examples.

Compounds of the invention may also be prepared as a pharmaceutically acceptable acid addition salt by reacting the free base form of the compound with a pharmaceutically acceptable inorganic or organic acid. Alternatively, a pharmaceutically acceptable base addition salt of a compound of the invention may be prepared by reacting the free acid form of the compound with a pharmaceutically acceptable inorganic or organic base. Alternatively, salt forms of the compounds of the invention may be prepared using salts of the starting materials or intermediates.

The free acid or free base forms of the compounds of the invention may be prepared from the corresponding base addition salt or acid addition salt form, respectively. For example a compound of the invention in an acid addition salt form may be converted to the corresponding free base by treating with a suitable base (e.g., ammonium hydroxide solution, sodium hydroxide, and the like). A compound of the invention in a base addition salt form may be converted to the corresponding free acid by treating with a suitable acid (e.g., hydrochloric acid, etc.).

Compounds of the invention in unoxidized form may be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. acetonitrile, ethanol, aqueous dioxane, or the like) at 0 to 80° C.

Protected derivatives of the compounds of the invention may be made by means known to those of ordinary skill in the alt. A detailed description of techniques applicable to the creation of protecting groups and their removal may be found in T. W. Greene, "Protecting Groups in Organic Chemistry", 3$^{rd}$ edition, John Wiley and Sons, Inc., 1999.

Compounds of the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

The invention also provides prodrug derivatives of the compounds of the invention. Conversion of prodrug derivatives to the compounds of the invention may occur under physiological conditions as described in "Pharmaceutical Development", vol. 7 (Molecular Design), pp. 163-198 (1990), or with a reaction by an enzyme, a gastric acid, etc. in the living body (e.g., conversion by enzymatic oxidation, reduction, hydrolysis, etc.).

Prodrug derivatives of the compounds of the invention may be prepared by methods known to those of ordinary skill in the art (e.g., Saulnier et al., (1994), Bioorganic and Medicinal Chemistry Letters, Vol. 4, p. 1985). For example, appropriate prodrugs may be prepared by reacting a non-derivatized compound of the invention with a suitable carbamylating agent (e.g., 1,1-acyloxyalkylcarbanochloridate, para-nitrophenyl carbonate, or the like). Other examples include compounds of the invention wherein an amino group is substituted with acyl, alkyl, phosphoric acid, etc. (e.g., substitution of an amino group with eicosanyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, tert-butyl, etc,); a compound wherein a hydroxy group is substituted with acyl, alkyl, phosphoric acid, boric acid, etc. (e.g., substitution of a hydroxyl group with acetyl, palmitoyl, propanoyl, pivaloyl, succinyl, fumaryl, alanyl, dimethylaminomethylcarbonyl, etc.); a compound wherein a carboxyl group is substituted with ester, amide, etc. (e.g., modification of a carboxyl group with ethyl ester, phenyl ester, carboxymethyl ester, dimethylaminomethyl ester, pivaloyloxymethyl ester, ethoxycarbonyloxyethyl ester, phthalidyl ester, (5-methyl-2-oxo-1,3-dioxolen-4-yl)methyl ester, cyclohexyloxycarbonylethyl ester, methyl amide, etc.); etc. In particular examples, the prodrug derivatives are prepared by esterification of a carboxyl group with a C1-6 alkyl group such as methyl, ethyl, tert-butyl and the like.

Compounds of the invention may be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers may be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and may be readily separated by taking advantage of these dissimilarities. The diastereomers may be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture may be found in Jean Jacques, Andre Collet, Samuel H. Wilen, "Enantiomers, Racemates and Resolutions", John Wiley And Sons, Inc., 1981.

The compounds of the invention may be prepared as exemplified in the Examples, and may optionally involve:

(a) converting a compound of the invention into a pharmaceutically acceptable salt;

(b) converting a salt form of a compound of the invention to a non-salt form;

(c) converting an unoxidized form of a compound of the invention into a pharmaceutically acceptable N-oxide;

(d) converting an N-oxide form of a compound of the invention to its unoxidized form;

(e) resolving an individual isomer of a compound of the invention from a mixture of isomers;

(f) converting a non-derivatized compound of the invention into a pharmaceutically acceptable prodrug derivative; and (g) converting a prodrug derivative of a compound of the invention to its non-derivatized form.

Insofar as the production of the starting materials is not particularly described, the compounds are known or may be prepared analogously to methods known in the art or as disclosed in the Examples hereinafter. One of skill in the art will appreciate that the synthetic methodologies described herein are only representative of methods for preparation of the compounds of the present invention, and that other well known methods may similarly be used. The present invention is further exemplified, but not limited, by the following Examples that illustrate the preparation of the compounds of the invention.

Preparation of Intermediates (4-(2-chlorophenyl)thiazol-2-yl)methyl methanesulfonate (4)

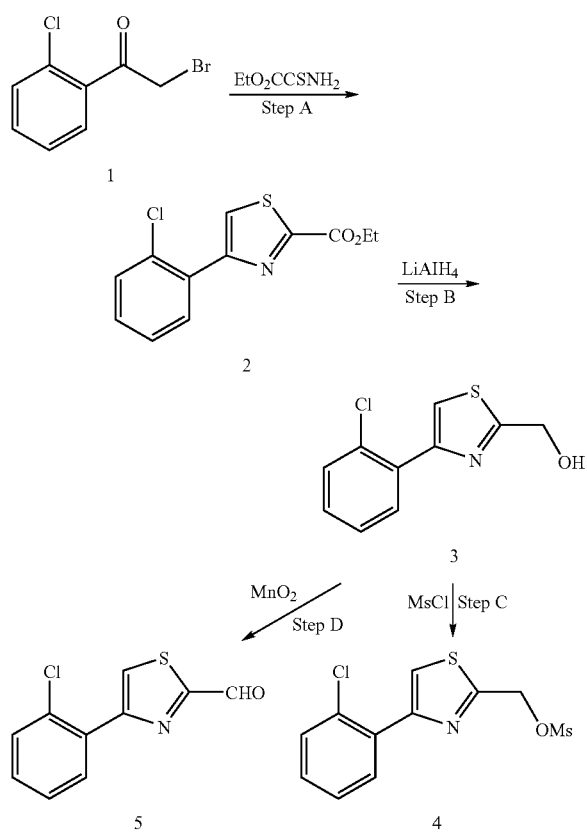

Step A: 2-Bromo-1-(2-chloro-phenyl)-ethanone (20.0 g, 1.0 eq, 85.7 mmol) is dissolved in EtOH (100 ml). Ethyl thioxamate (11.4 g, 1 eq, 85.7 mmol) is added and the mixture is heated to reflux for 6 hours. The reaction is then cooled, and ethanol is evaporated and replaced with EtOAc. The solution is washed with saturated $NaHCO_3$, water and brine. The combined filtrates are dried over $MgSO_4$, concentrated and purified by silica chromatography (0-20% EtOAc in hexanes) to give the ester 2 as a dark solid: $^1$H-NMR (400 MHz, $CDCl_3$) δ=8.08 (s, 1H), 7.97 (m, 1H), 7.74 (m, 1H), 7.33 (m, 1H), 4.51 (q, J=9.6 Hz, 2H), 1.45 (t, J=9.6 Hz, 3H). MS calcd. For $C_{12}H_{10}ClNO_2S$ (M+H$^+$) 268.0. found 268.0.

Step B: The ester 2 from Step A above (13.88 g, 51.8 mmol) is dissolved in anhydrous THF (200 mL) and cooled to 0° C. under nitrogen. Lithium tetrahydroaluminate in THF (1.0 M, 62 mL, 62 mmol) is added dropwise with stirring, over a 10 min period. After the addition, the mixture is stirred at 0° C. for 30 min. Saturated $Na_2SO_4$ aqueous solution is added at 0° C., dropwise, with stirring, until all gas evolution ceased (about 8 mL). The mixture is diluted with more THF (200 mL) and filtered. The solids are suspended in methanol (150 mL) and filtered again. The combined filtrates are dried over $MgSO_4$ and concentrated. Silica gel chromatography (0 to 100% EtOAc in hexanes) yielded (4-(2-chlorophenyl)thiazol-2-yl)methanol 3 as a light-brown solid: $^1$H-NMR (400 MHz, $CDCl_3$) δ=7.90 (dd, J=1.8, 7.7 Hz, 1H), 7.80 (s, 1H), 7.47 (dd, J=1.4, 7.9 Hz, 1H), 7.34 (ddd, J=1.4, 7.6, 7.9 Hz, 1H), 7.29 (ddd, J=1.9, 7.7, 7.7 Hz, 1H), 5.02 (s, 2H), 2.68 (br. s, 1H). MS calcd. for $C_{10}H_9ClNOS$ (M+H$^+$) 226.0. found 226.0.

Step C: (4-(2-chlorophenyl)thiazol-2-yl)methanol 3 (0.41 g, 1.82 mmol) is dissolved in dichloromethane (25 mL). Triethylamine (0.50 mL, 3.56 mmol) is added and the solution is cooled to 0° C. Methanesulfonyl chloride (0.17 mL, 2.19 mmol) is added dropwise to the cooled solution, with stirring. The bath is removed and the mixture is stirred at room temperature for 3 h. Addition of water, extraction with DCM, drying over $MgSO_4$ and concentration yielded (4-(2-chlorophenyl)thiazol-2-yl)methyl methanesulfonate 4 as an oil: $^1$H-NMR (400 MHz, $CDCl_3$) δ=7.93 (s, 1H) 7.90 (dd, J=1.9, 7.7 Hz, 1H), 7.48 (dd, J=1.4, 7.7 Hz, 1H), 7.36 (ddd, J=1.4, 7.4, 7.6 Hz, 1H), 7.30 (ddd, J=1.9, 7.7, 7.5 Hz, 1H), 5.56 (s, 2H), 3.13 (s, 3H). MS calcd. for $C_{11}H_{11}ClNO_3S_2$ (M+H$^+$) 304.0. found 303.9.

4-(2-chlorophenyl)thiazole-2-carbaldehyde (5)

Step D: (4-(2-Chlorophenyl)thiazol-2-yl)methyl methanesulfonate 4 from Step C above (0.10 g, 0.51 mmol) is dissolved in dichloromethane (4.0 mL), followed by addition of manganese dioxide (0.18 g, 2 mmol). The suspension is vigorously stirred at room temperature overnight. Filtration and concentration yielded 4-(2-chlorophenyl)thiazole-2-carbaldehyde 5 as a light-brown oil: MS calcd. for $C_{10}H_7ClNOS$ (M+H$^+$) 224.0. found 224.0.

2-Bromomethyl-5-(2-chloro-phenyl)-thiazole (7)

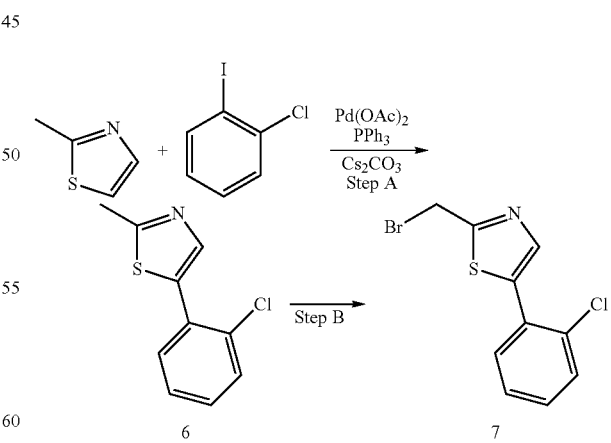

Step A: 1-chloro-2-iodobenzene (500 μL, 4.1 mmol) is dissolved in DMF (10 mL), then 2-methylthiazole (406 mg, 4.1 mmol), triphenylphosphine (54 mg, 0.20 mmol), cesium carbonate (1.33 g, 4.1 mmol), palladium(II) acetate (92 mg, 0.41 mmol) are added and the mixture is stirred at 140° C. for 24 h. The reaction mixture is diluted with 1 M HCl (10 mL) and extracted into EtOAc (3×10 mL). The organic layers are combined and washed with H$_2$O (2×20 mL) and brine (10 mL), then dried (MgSO$_4$), filtered, concentrated and purified by silica gel chromatography (EtOAc/hexane, gradient) to give 5-(2-chlorophenyl)-2-methylthiazole 6. $^1$H-NMR (400 MHz, CDCl$_3$) δ=7.80 (s, 1H), 7.48 (m, 2H), 7.28 (m, 2H), 2.75 (s, 3H). MS calcd. for C$_{10}$H$_9$ClNS (M+H$^+$) 210.0. found 210.1.

Step B: N-Bromosuccinimide (344 mg, 1.61 mmol) is added to a solution of 5-(2-chlorophenyl)-2-methylthiazole (337 mg, 1.93 mmol) in carbon tetrachloride (15 mL). The above solution is stirred at 75° C. for 18 h. The solution is diluted with CH$_2$Cl$_2$ (50 mL) and washed with saturated NaHCO$_3$ (50 mL) and brine (30 mL). The organic layer is dried (MgSO$_4$), filtered, concentrated and purified by silica gel chromatography (EtOAc/hexane, gradient) to give 2-(bromomethyl)-5-(2-chlorophenyl)thiazole 7 as a white solid. MS calcd. for C$_{10}$H$_8$BrClNS (M+H+) 287.9. found 286.9.

Intermediates 8-14

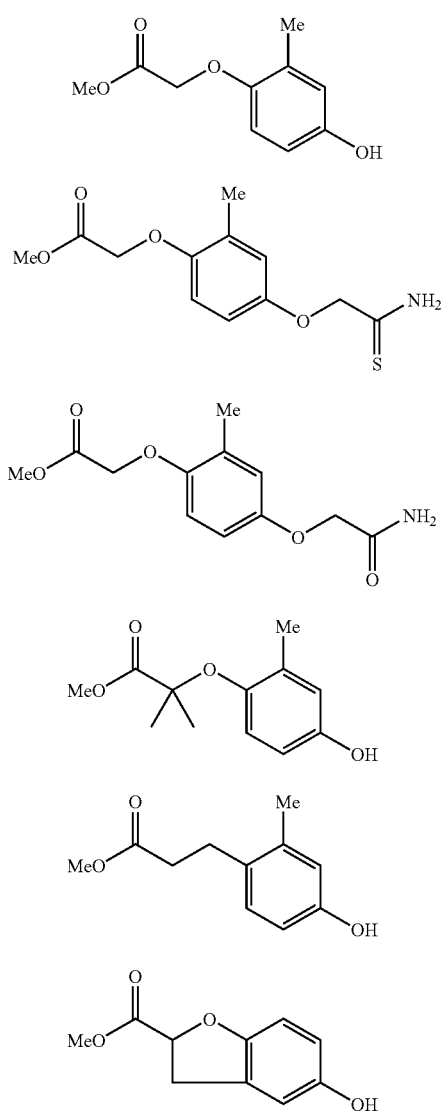

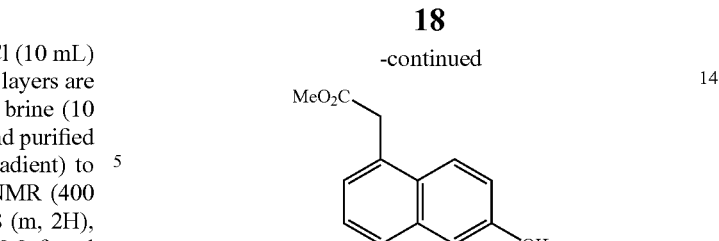

The syntheses of non-commercially available intermediates 8-14 are described in WO 2005116000, incorporated herein by reference in its entirety.

EXAMPLE 1

2-(4-((4-(2-Bromophenyl)thiazol-2-yl)methoxy)-2-methylphenoxy)acetic acid (A1)

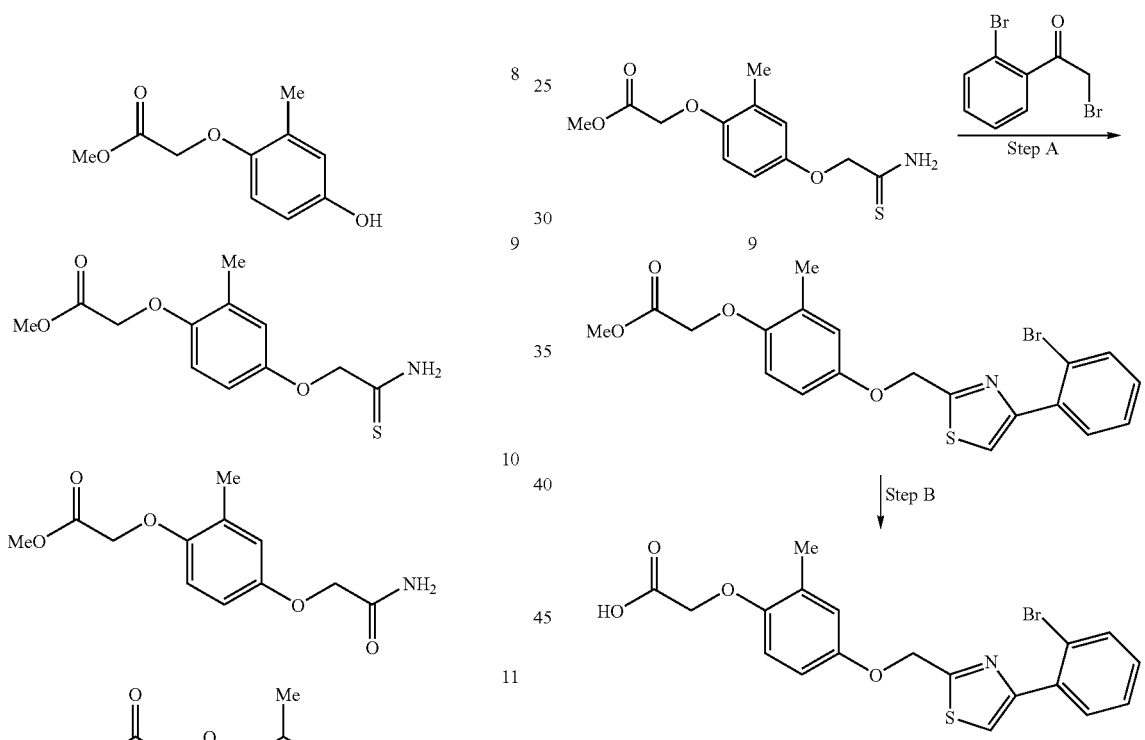

Step A: Intermediate 9 (1.0 g, 3.73 mmol), and 2-bromophenacyl bromide (1.03 g, 3.73 mmol) are heated at reflux in MeOH (20 mL) for 12 hours. The mixture is cooled, extracted with EtOAc (2×40 mL) and washed with saturated NaHCO$_3$ (20 mL), then H$_2$O (20 mL). The organic layer is dried (MgSO$_4$), filtered, and concentrated. The residue is triturated with hexanes and filtered to give methyl 2-(4-((4-(2-bromophenyl)thiazol-2-yl)methoxy)-2-methylphenoxy) acetate as a white powder: $^1$H-NMR (400 MHz, CDCl$_3$) δ=7.77 (dd, J=1.6, 7.6 Hz, 1H), 7.75 (s, 1H), 7.68 (dd, J=1.2, 8.0 Hz, 1H), 7.39 (dt, J=1.2, 7.6 Hz, 1H), 7.21 (dt, J=1.6, 8.0 Hz, 1H), 6.89 (d, J=2.8 Hz, 1H), 6.78 (dd, J=2.8, 8.8 Hz, 1H), 6.67 (d, J=8.8 Hz, 1H), 5.37 (s, 2H), 4.61 (s, 2H), 3.80 (s, 3H), 2.29 (s, 3H). MS calcd. for C$_{19}$H$_{17}$BrNO$_4$S (M+H$^+$) 448.0. found 447.9.

Step B: Methyl 2-(4-((4-(2-bromophenyl)thiazol-2-yl)methoxy)-2-methylphenoxy)acetate (20 mg, 0.04 mmol) is dissolved in THF (1 mL). A solution of 1 M LiOH in H$_2$O (0.2 mL) is added, and the mixture is stirred for 1 h at rt. The mixture is acidified with 1 M HCl (0.25 mL); EtOAc (10 mL) is added and the organic layer is washed with brine (5 mL). The organic layer is dried (MgSO$_4$), filtered, concentrated and purified on reverse phase HPLC (H$_2$O/MeCN gradient) to afford the title compound A1 as a white solid: $^1$H-NMR (400 MHz, CDCl$_3$) δ=7.74 (dd, J=1.6, 8.0 Hz, 1H), 7.73 (s, 1H), 7.67 (dd, J=1.2, 8.0 Hz, 1H), 7.38 (dt, J=1.2, 7.6 Hz, 1H), 7.22 (dt, J=1.6, 7.6 Hz, 1H), 6.90 (d, J=2.8 Hz, 1H), 6.78 (dd, J=2.8, 8.8 Hz, 1H), 6.70 (d, J=8.8 Hz, 1H), 5.37 (s, 2H), 4.63 (s, 2H), 2.28 (s, 3H). MS calcd. for C$_{19}$H$_{17}$BrNO$_4$S (M+H$^+$) 434.0. found 433.9.

EXAMPLE 2

2-(4-((4-(2-cyclopropylphenyl)thiazol-2-yl)methoxy)-2-methylphenoxy)acetic acid (B1)

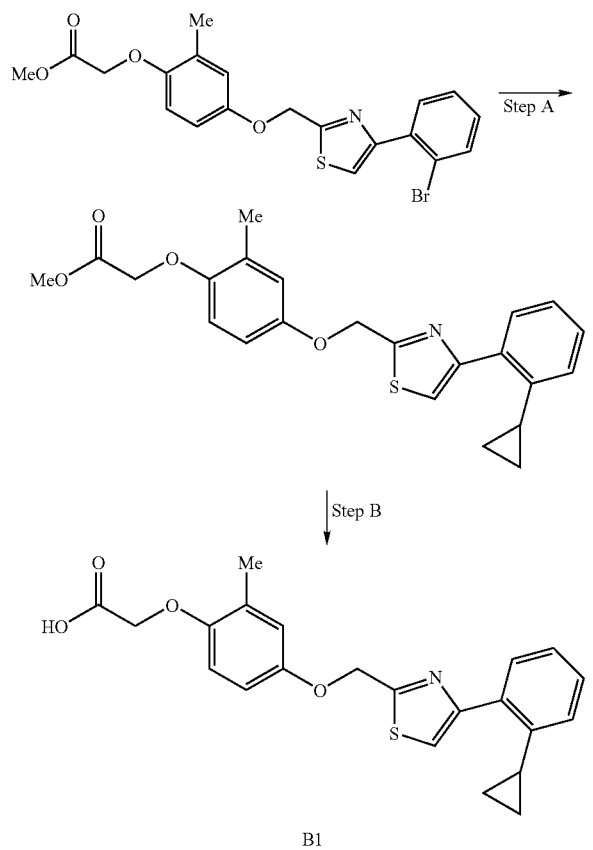

B1

Step A: {4-[4-(2-Bromo-phenyl)-thiazol-2-ylmethoxy]-2-methyl-phenoxy}-acetic acid methyl ester (30 mg, 0.067 mmol), cyclopropylboronic acid (6.9 mg, 0.080 mmol) and sodium carbonate (21 mg, 0.20 mmol) are dissolved in water (120 μL), ethanol (90 μL) and 1,2-dimethoxyethane (360 μL). Pd(PPh$_3$)$_4$ (10 mol %) is added, and the mixture is subjected to microwave (180° C.) for 5 min in a sealed tube to give crude methyl 2-(4-((4-(2-cyclopropylphenyl)thiazol-2-yl)methoxy)-2-methylphenoxy)acetate, which is used without further purification in Step B.

Step B: The solution of methyl 2-(4-((4-(2-cyclopropylphenyl)thiazol-2-yl)methoxy)-2-methylphenoxy)acetate from Step A is diluted with THF (1 mL), then a solution of 1 M LiOH in H$_2$O (0.2 mL) is added and the mixture is stirred for 3 h at rt. The mixture is acidified with 1 M HCl (0.25 mL), EtOAc (10 mL) is added and the organic layer washed with brine (5 mL). The organic layer is dried (MgSO$_4$), filtered, concentrated and purified on reverse phase HPLC (H$_2$O/MeCN gradient) to afford the title compound B1 as a white solid: $^1$H-NMR (400 MHz, CDCl$_3$) δ=7.57 (dd, J=1.6, 7.6 Hz, 1H), 7.48 (s, 1H), 7.30 (dt, J=1.6, 7.6 Hz, 1H), 7.24 (dt, J=1.2, 7.2 Hz, 1H), 7.03 (d, J=7.6 Hz, 1H), 6.90 (d, J=2.8 Hz, 1H), 6.78 (dd, J=2.8, 8.8 Hz, 1H), 6.69 (d, J=8.8 Hz, 1H), 5.41 (s, 2H), 4.62 (s, 2H), 2.28 (s, 3H), 2.10 (m, 1H), 0.89 (m, 2H), 0.72 (m, 2H). MS calcd. for C$_{22}$H$_{22}$NO$_4$S (M+H$^+$) 396.1. found 396.1.

EXAMPLE 3

2-(4-((4-(3-(cyclopentyloxy)phenyl)thiazol-2-yl)methoxy)-2-methylphenoxy)acetic acid (C1)

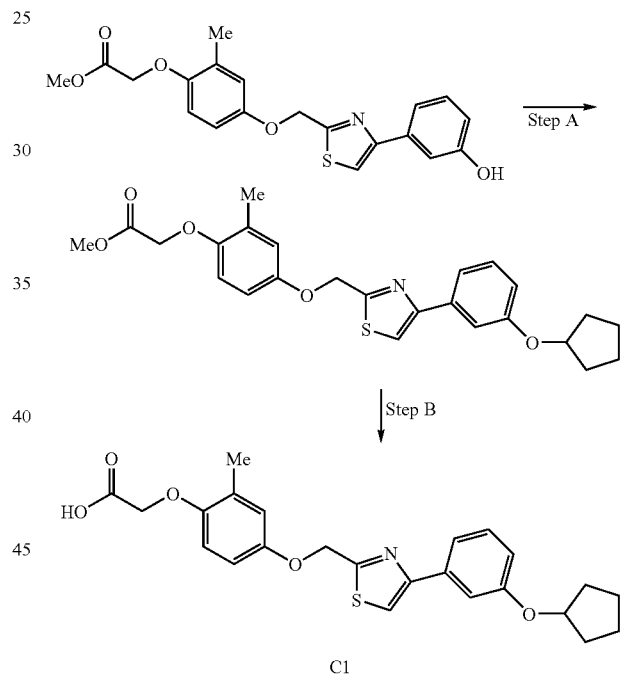

C1

Step A: 2-(4-((4-(3-hydroxyphenyl)thiazol-2-yl)methoxy)-2-methylphenoxy)acetic acid (20 mol, 0.052 mmol) is dissolved in acetone (4 mL). K$_2$CO$_3$ (21 mg, 0.156 mmol) is added, followed by cyclopentyl bromide (38 μL, 0.259 mmol) and the resulting mixture is heated to reflux for 18 h. The solvent is evaporated in vacuo to give crude methyl 2-(4-((4-(3-(cyclopentyloxy)phenyl)thiazol-2-yl)methoxy)-2-methylphenoxy)acetate, which is used in Step B without further purification.

Step B: The methyl 2-(4-((4-(3-(cyclopentyloxy)phenyl)thiazol-2-yl)methoxy)-2-methylphenoxy)acetate from Step A is dissolved in THF (1 mL), then a solution of 1 M LiOH in H$_2$O (0.2 mL) is added and the mixture is stirred for 3 h at rt. The mixture is acidified with 1 M HCl (0.25 mL). EtOAc (10 mL) is added, and the organic layer is washed with brine (5 mL). The organic layer is dried (MgSO$_4$), filtered, concentrated and purified on reverse phase HPLC (H₂O/MeCN gradient) to afford the title compound C1 as a white solid: ¹H-NMR (400 MHz, CDCl₃) δ=7.46 (s, 1H), 7.33 (m, 3H), 6.89 (m, 2H), 6.76 (dd, J=2.8, 8.8 Hz, 1H), 6.69 (d, J=8.8 Hz, 1H), 5.41 (s, 2H), 4.84 (m, 1H), 4.64 (s, 2H), 2.28 (s, 3H), 1.88 (m, 4H), 1.82 (m, 2H), 1.63 (m, 2H). MS calcd. for $C_{24}H_{26}NO_5S$ (M+H⁺) 440.2. found 440.1.

EXAMPLE 4

2-(4-((4-(2-chlorophenyl)oxazol-2-yl)methoxy)-2-methylphenoxy)acetic acid (D1)

1H), 5.10 (s, 2H), 4.57 (s, 2H), 2.21 (s, 3H). MS calcd. for $C_{19}H_{17}ClNO_5$ (M+H⁺) 374.1. found 374.1.

EXAMPLE 5

2-(4-((5-(2-chlorophenyl)thiazol-2-yl)methoxy)-2-methylphenoxy)acetic acid (E1)

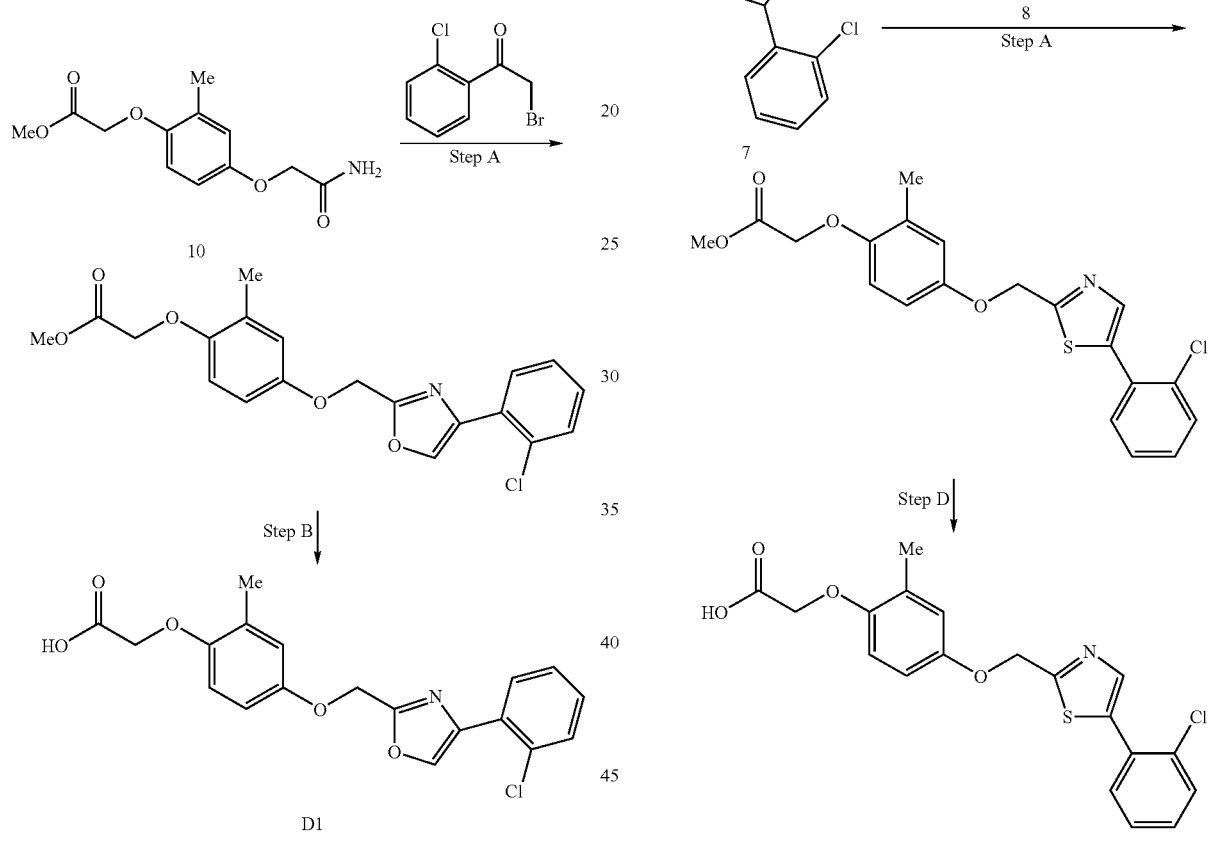

Step A: Intermediate 10 (50 mg, 0.197 mmol), and 2-chlorophenacyl bromide (230 μL, 0.985 mmol) are heated with stirring at 120° C. for 12 hours. The crude mixture containing methyl 2-(4-((4-(2-chlorophenyl)oxazol-2-yl)methoxy)-2-methylphenoxy)acetate is used directly in Step B without purification.

Step B: The solution of methyl 2-(4-((4-(2-chlorophenyl)oxazol-2-yl)methoxy)-2-methylphenoxy)acetate from Step A is diluted with THF (1 mL), then a solution of 1 M LiOH in H₂O (0.2 mL) is added and the mixture is stirred for 12 h at rt. The mixture is acidified with 1 M HCl (5 mL), and extracted into EtOAc (20 mL). The organic layer is dried (MgSO₄), filtered, concentrated and purified on reverse phase HPLC (H₂O/MeCN gradient) to afford the title compound D1 as a white solid: ¹H-NMR (400 MHz, CDCl₃) δ=8.28 (s, 1H), 7.97 (dd, J=0.8, 8.0 Hz, 1H), 7.38 (dd, J=0.8, 7.6 Hz, 1H), 7.29 (t, J=7.6 Hz, 1H), 7.20 (dt, J=1.2, 7.6 Hz, 1H), 6.82 (d, J=2.4 Hz, 1H), 6.73 (dd, J=2.8, 8.8 Hz, 1H), 6.63 (d, J=8.8 Hz, 1H), Step A: Intermediate 8 (34 mg, 0.17 mmol) and Cs₂CO₃ (113 mg, 0.34 mmol) are added to a solution of intermediate 7 (50 mg, 0.17 mmol) in MeCN (5 mL). The mixture is stirred for 3 h at rt. The crude mixture containing methyl 2-(4-((5-(2-chlorophenyl)thiazol-2-yl)methoxy)-2-methylphenoxy) acetate is used directly in Step D without purification.

Step B: The solution of methyl 2-(4-((5-(2-chlorophenyl)thiazol-2-yl)methoxy)-2-methylphenoxy)acetate from Step A is treated with a solution of 1 M LiOH in H₂O (1 mL), and the mixture is stirred for 12 h at rt. The mixture is acidified with 1 M HCl (10 mL) and extracted with EtOAc (20 mL). The organic layer is dried (MgSO₄), filtered, concentrated and purified on reverse phase HPLC(H₂O/MeCN gradient) to afford the title compound E1 as a white solid: ¹H-NMR (400 MHz, CDCl₃) δ=7.96 (s, 1H), 7.50 (m, 2H), 7.30 (m, 2H), 6.89 (d, J=2.4 Hz, 1H), 6.77 (dd, J=2.4, 8.8 Hz, 1H), 6.71 (d, J=8.8 Hz, 1H), 5.33 (s, 2H), 4.64 (s, 2H), 2.29 (s, 3H). MS calcd. for $C_{19}H_{17}ClNO_4S$ (M+H⁺) 390.0. found 390.0.

EXAMPLE 6

{4-[4-(2-Chloro-phenyl)-thiazol-2-ylmethoxy]-2-methyl-phenoxy}-acetic acid (F1)

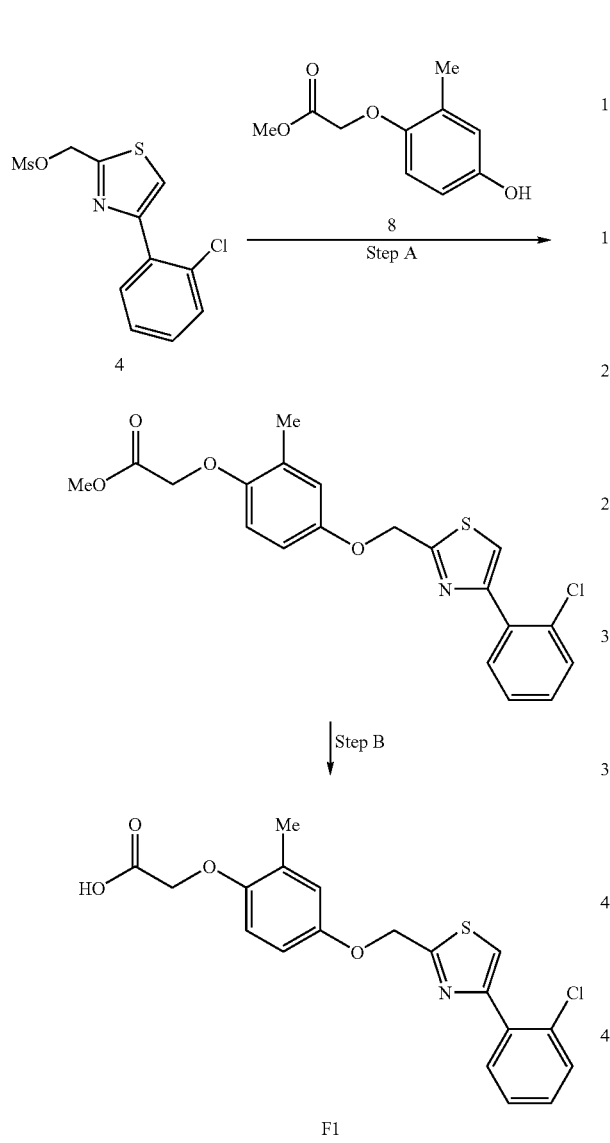

F1

Step A: Intermediate 8 (34 mg, 0.17 mmol) and Cs₂CO₃ (113 mg, 0.34 mmol) are added to a solution of intermediate 4 (52 mg, 0.17 mmol) in MeCN (5 mL). The mixture is stirred for 3 h at rt. The crude mixture containing {4-[4-(2-chloro-phenyl)-thiazol-2-ylmethoxy]-2-methyl-phenoxy}-acetic acid methyl ester is used directly in Step B without purification.

Step B: The solution of {4-[4-(2-chloro-phenyl)-thiazol-2-ylmethoxy]-2-methyl-phenoxy}-acetic acid methyl ester from Step C is treated with a solution of 1 M LiOH in H₂O (1 mL), and the mixture is stirred for 12 h at rt. The mixture is acidified with 1 M HCl (1.2 mL) and extracted into EtOAc (20 mL). The organic layer is dried (MgSO₄), filtered, concentrated and purified on reverse phase HPLC (H₂O/MeCN gradient) to afford the title compound F1 as a white solid: MS calcd. for $C_{19}H_{17}ClNO_4S$ (M+H⁺) 390.0. found 390.0.

EXAMPLE 7

6-{[4-(2-Chloro-phenyl)-thiazol-2-ylmethyl]-amino}-naphthalene-2-carboxylic acid (G1)

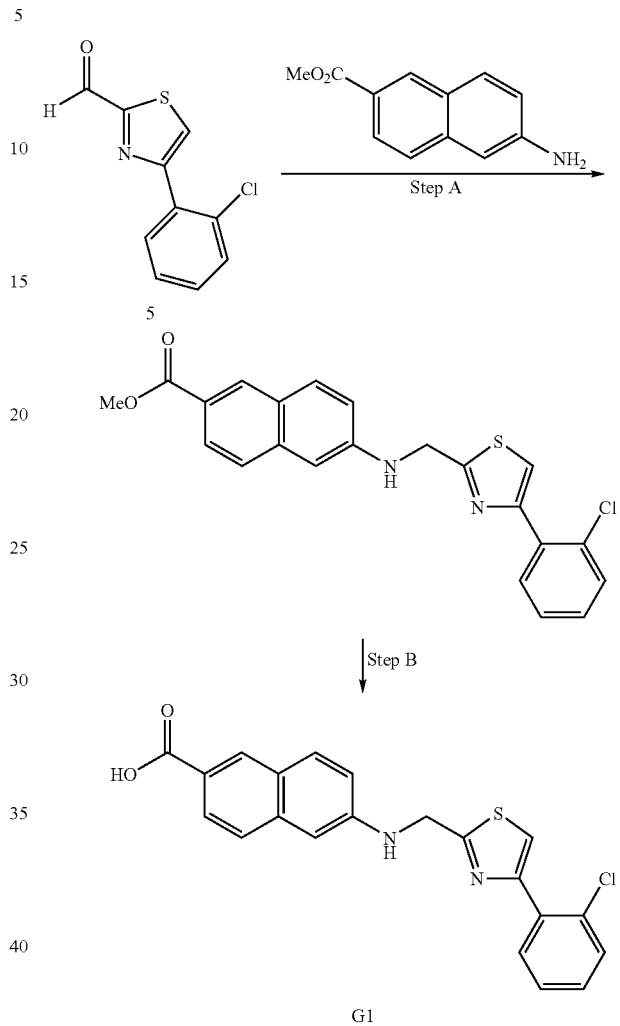

G1

Step A: A solution of 6-amino-naphthalene-2-carboxylic acid methyl ester (241 mg, 1.2 mmol) and intermediate 5 (224 mg, 1 mmol) in DCM (15 mL) is stirred at rt with Na₂SO₄ (0.2 g, 1.4 mmol) for 1 h. Sodium triacetoxyborohydride (636 mg, 3 mmol) is added and the mixture is stirred for 16 h at rt. H₂O (10 mL) is added and the product is extracted with DCM (3×10 mL). The organic layers are combined, dried (Na₂SO₄), filtered and concentrated. The crude 6-{[4-(2-chloro-phenyl)-thiazol-2-ylmethyl]-amino}-naphthalene-2-carboxylic acid methyl ester is used in the next step without further purification.

Step B: The crude 6-{[4-(2-chloro-phenyl)-thiazol-2-ylmethyl]-amino}-naphthalene-2-carboxylic acid methyl ester from Step A is dissolved in THF (1 mL). A solution of 1 M LiOH in H₂O (1 mL) is added and the mixture is stirred for 12 h at rt. The mixture is acidified with 1 M HCl (1 mL) and extracted into EtOAc (20 mL). The organic layer is dried (MgSO₄), filtered, concentrated and purified on reverse phase HPLC (H₂O/MeCN gradient) to afford the title compound G1 as a white solid: MS calcd. for $C_{21}H_{16}ClN_2O_2S$ (M+H⁺) 395.9. found 396.0.

Representative compounds of the invention, prepared by following procedures described in the above examples using appropriate starting materials that will be apparent to those skilled in the art, are shown in Table 1.

TABLE 1

| | Compound Structure | Physical Data<br>¹H NMR 400 MHz (DMSO-d₆)<br>and/or MS (m/z) |
|---|---|---|
| A1 | 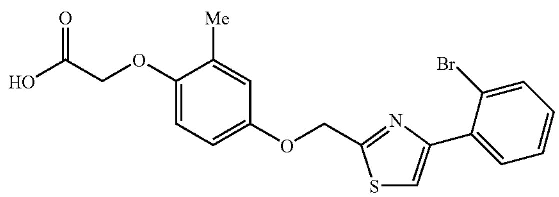 [SMILES: Cc1cc(OCc2nc(-c3ccccc3Br)cs2)ccc1OCC(=O)O] | ¹H-NMR (400 MHz, CDCl₃) δ = 7.74 (dd, J = 1.6, 8.0 Hz, 1H). 7.73 (s, 1H), 7.67 (dd, J = 1.2, 8.0 Hz, 1H), 7.38 (dt, J = 1.2, 7.6 Hz, 1H), 7.22 (dt, J = 1.6, 7.6 Hz, 1H), 6.90 (d, J = 2.8 Hz, 1H), 6.78 (dd, J = 2.8, 8.8 Hz, 1H), 6.70 (d, J = 8.8 Hz, 1H), 5.37 (s, 2H), 4.63 (s, 2H), 2.28 (s, 3H). MS calcd. for C₁₉H₁₇BrNO₄S (M + H⁺) 434.0, found 433.9. |
| A2 | 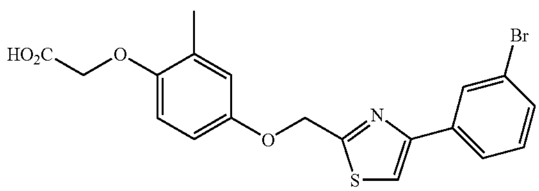 [SMILES: Cc1cc(OCc2nc(-c3cccc(Br)c3)cs2)ccc1OCC(=O)O] | ¹H-NMR (400 MHz, DMSO-d6) δ = 8.30 (s, 1H), 8.17 (t, J = 2.0 Hz, 1H), 7.98 (d, J = 8.0 Hz, 1H), 7.56 (m, 1H), 7.43 (t, J = 8.0 Hz, 1H), 6.95 (d, J = 2.8 Hz, 1H), 6.85 (dd, J = 2.8, 8.8 Hz, 1H), 6.77 (d, J = 8.8 Hz, 1H), 5.42 (s, 2H), 4.61 (s, 2H), 2.19 (s, 3H). MS calcd. for C₁₉H₁₇BrNO₄S (M + H⁺) 434.0, found 433.9. |
| A3 | 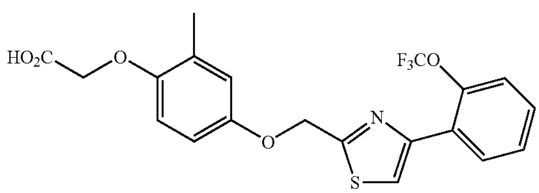 [SMILES: Cc1cc(OCc2nc(-c3ccccc3OC(F)(F)F)cs2)ccc1OCC(=O)O] | ¹H-NMR (400 MHz, DMSO-d6) δ = 8.11 (m, 1H), 7.99 (s, 1H), 7.52 (m, 3H), 6.95 (d, J = 2.8 Hz, 1H), 6.85 (dd, J = 2.8, 8.8 Hz, 1H), 6.78 (d, J = 8.8 Hz, 1H), 5.42 (s, 2H), 4.63 (s, 2H), 2.19 (s, 3H). MS calcd. for C₂₀H₁₇F₃NO₅S (M + H⁺) 440.1, found 440.1. |
| A4 | 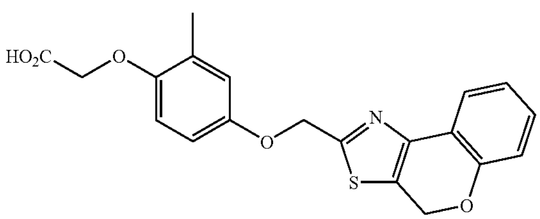 [SMILES: Cc1cc(OCc2nc3c(s2)COc2ccccc2-3)ccc1OCC(=O)O] | ¹H-NMR (400 MHz, DMSO-d6) δ = 7.83 (dd, J = 1.6, 7.6 Hz, 1H), 7.22 (dt, J = 1.2, 7.6 Hz, 1H), 7.05 (t, J = 7.2 Hz, 1H), 6.95 (dd, J = 0.8, 8.0 Hz, 1H), 6.88 (d, J = 2.8 Hz, 1H), 6.78 (dd, J = 2.8, 8.8 Hz, 1H), 6.70 (d, J = 8.8 Hz, 1H), 5.45 (s, 2H), 5.38 (s, 2H), 4.64 (s, 2H), 2.28 (s, 3H). MS calcd. for C₂₀H₁₈NO₅S (M + H⁺) 384.1, found 384.0. |
| A5 | 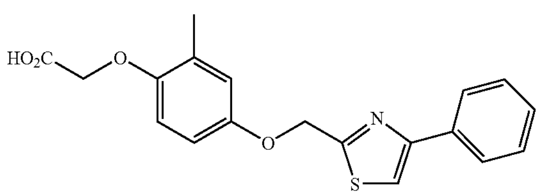 [SMILES: Cc1cc(OCc2nc(-c3ccccc3)cs2)ccc1OCC(=O)O] | MS calcd. for C₁₉H₁₈NO₄S (M + H⁺) 356.1, found 356.1. |
| A6 | 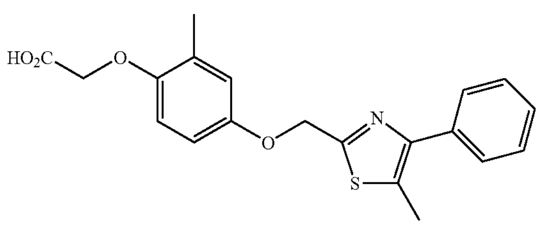 [SMILES: Cc1cc(OCc2nc(-c3ccccc3)c(C)s2)ccc1OCC(=O)O] | MS calcd. for C₂₀H₂₀NO₄S (M + H⁺) 370.1, found 370.1. |
| A7 | 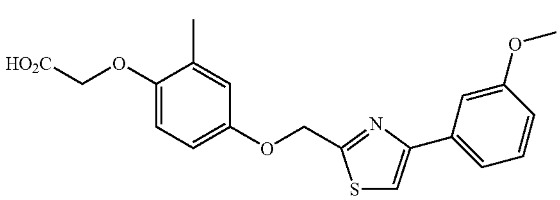 [SMILES: COc1cccc(-c2csc(COc3ccc(OCC(=O)O)c(C)c3)n2)c1] | MS calcd. for C₂₀H₂₀NO₅S (M + H⁺) 386.1, found 386.1. |

TABLE 1-continued

| | Compound Structure | Physical Data<br>$^1$H NMR 400 MHz (DMSO-$d_6$)<br>and/or MS (m/z) |
|---|---|---|
| A8 | 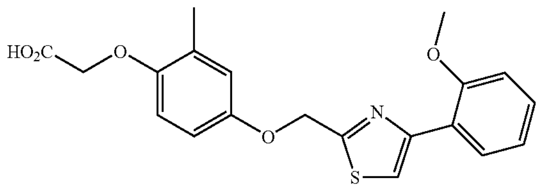 [SMILES: COc1ccccc1-c1csc(COc2ccc(OCC(=O)O)c(C)c2)n1] | MS calcd. for $C_{20}H_{20}NO_5S$ (M + H$^+$) 386.1, found 386.1. |
| A9 | 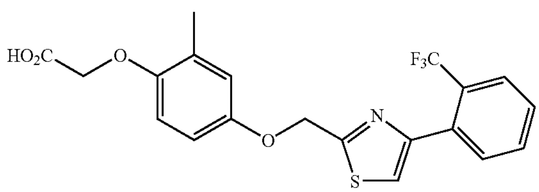 [SMILES: Cc1cc(OCc2nc(-c3ccccc3C(F)(F)F)cs2)ccc1OCC(=O)O] | MS calcd. for $C_{20}H_{17}F_3NO_4S$ (M + H$^+$) 424.1, found 424.1. |
| A10 | 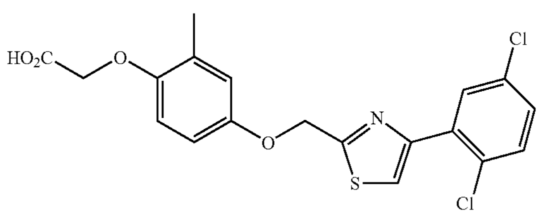 [SMILES: Cc1cc(OCc2nc(-c3cc(Cl)ccc3Cl)cs2)ccc1OCC(=O)O] | MS calcd. for $C_{19}H_{16}Cl_2NO_4S$ (M + H$^+$) 424.0, found 424.0. |
| B1 | 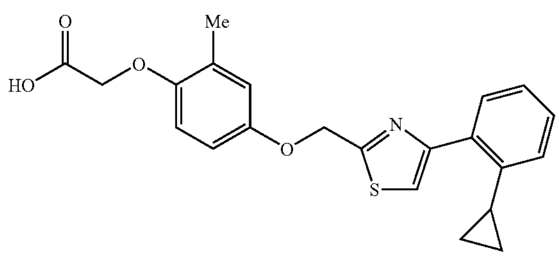 [SMILES: Cc1cc(OCc2nc(-c3ccccc3C3CC3)cs2)ccc1OCC(=O)O] | $^1$H-NMR (400 MHz, CDCl$_3$) δ = 7.57 (dd, J = 1.6, 7.6 Hz, 1H), 7.48 (s, 1H), 7.30 (dt, J = 1.6, 7.6 Hz, 1H), 7.24 (dt, J = 1.2, 7.2 Hz, 1H), 7.03 (d, J = 7.6 Hz, 1H), 6.90 (d, J = 2.8 Hz, 1H), 6.78 (dd, J = 2.8, 8.8 Hz, 1H), 6.69 (d, J = 8.8 Hz, 1H), 5.41 (s, 2H), 4.62 (s, 2H), 2.28 (s, 3H), 2.10 (m, 1H), 0.89 (m, 2H), 0.72 (m, 2H). MS calcd. for $C_{22}H_{22}NO_4S$ (M + H$^+$) 396.1, found 396.1. |
| C1 | 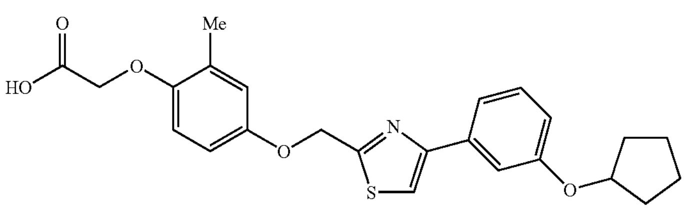 [SMILES: Cc1cc(OCc2nc(-c3cccc(OC4CCCC4)c3)cs2)ccc1OCC(=O)O] | $^1$H-NMR (400 MHz, CDCl$_3$) δ = 7.46 (s, 1H), 7.33 (m, 3H), 6.89 (m, 2H), 6.76 (dd, J = 2.8, 8.8 Hz, 1H), 6.69 (d, J = 8.8 Hz, 1H), 5.41 (s, 2H), 4.84 (m, 1H), 4.64 (s, 2H), 2.28 (s, 3H), 1.88 (m, 4H), 1.82 (m, 2H), 1.63 (m, 2H). MS calcd. for $C_{24}H_{26}NO_5S$ (M + H$^+$) 440.2, found 440.1. |
| D1 | 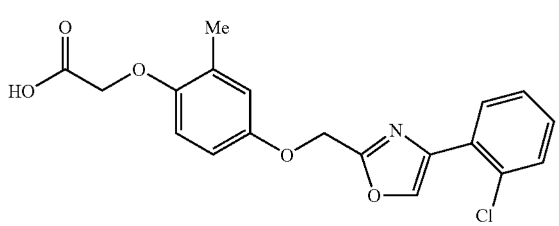 [SMILES: Cc1cc(OCc2nc(-c3ccccc3Cl)co2)ccc1OCC(=O)O] | $^1$H-NMR (400 MHz, CDCl$_3$) δ = 8.28 (s, 1H), 7.97 (dd, J = 0.8, 8.0 Hz, 1H), 7.38 (dd, J = 0.8, 7.6 Hz, 1H), 7.29 (t, J = 7.6 Hz, 1H), 7.20 (dt, J = 1.2, 7.6 Hz, 1H), 6.82 (d, J = 2.4 Hz, 1H), 6.73 (dd, J = 2.8, 8.8 Hz, 1H), 6.63 (d, J = 8.8 Hz, 1H), 5.10 (s, 2H), 4.57 (s, 2H), 2.21 (s, 3H). MS calcd. for $C_{19}H_{17}ClNO_5$ (M + H$^+$) 374.1, found 374.1. |
| D2 | 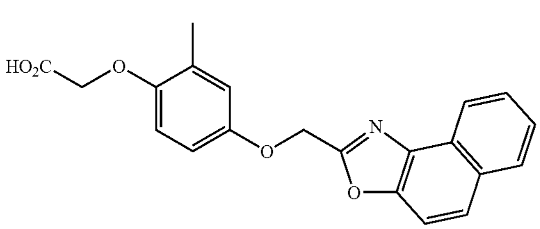 [SMILES: Cc1cc(OCc2nc3c(ccc4ccccc43)o2)ccc1OCC(=O)O] | MS calcd. for $C_{21}H_{18}NO_5$ (M + H$^+$) 364.1, found 364.1. |

TABLE 1-continued

| | Compound Structure | Physical Data<br>¹H NMR 400 MHz (DMSO-d₆)<br>and/or MS (m/z) |
|---|---|---|
| E1 | 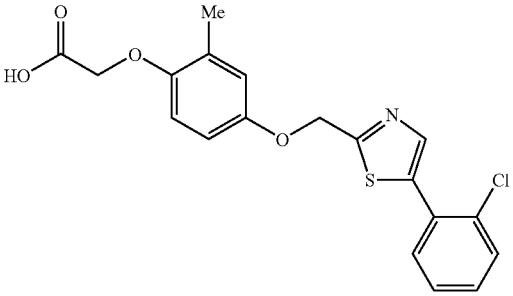 [SMILES: Cc1cc(OCc2ncc(-c3ccccc3Cl)s2)ccc1OCC(=O)O] | ¹H-NMR (400 MHz, CDCl₃) δ = 7.96 (s, 1H), 7.50 (m, 2H), 7.30 (m, 2H), 6.89 (d, J = 2.4 Hz, 1H), 6.77 (dd, J = 2.4, 8.8 Hz, 1H), 6.71 (d, J = 8.8 Hz, 1H), 5.33 (s, 2H), 4.64 (s, 2H), 2.29 (s, 3H). MS calcd. for C₁₉H₁₇ClNO₄S (M + H⁺) 390.0, found 390.0. |
| F1 | 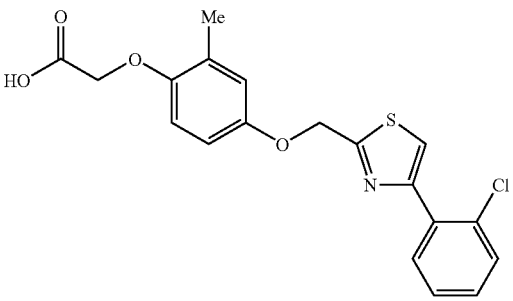 [SMILES: Cc1cc(OCc2nc(-c3ccccc3Cl)cs2)ccc1OCC(=O)O] | MS calcd. for C₁₉H₁₇ClNO₄S (M + H⁺) 390.0, found 390.0. |
| F2 | 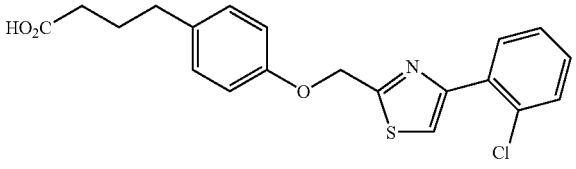 [SMILES: O=C(O)CCCc1ccc(OCc2nc(-c3ccccc3Cl)cs2)cc1] | MS calcd. for C₂₀H₁₉ClNO₃S (M + H⁺) 388.1, found 388.1. |
| F3 | 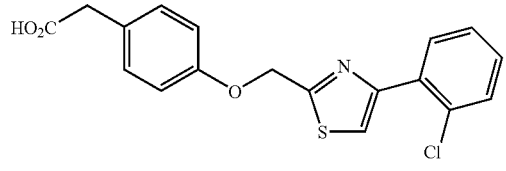 [SMILES: O=C(O)Cc1ccc(OCc2nc(-c3ccccc3Cl)cs2)cc1] | MS calcd. for C₁₈H₁₅ClNO₃S (M + H⁺) 360.0, found 360.0. |
| F4 | 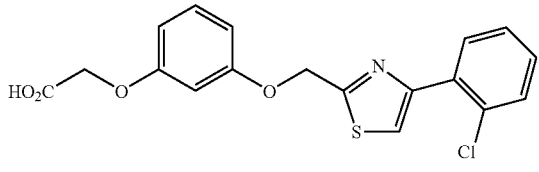 [SMILES: O=C(O)COc1cccc(OCc2nc(-c3ccccc3Cl)cs2)c1] | MS calcd. for C₁₈H₁₅ClNO₄S (M + H⁺) 376.0, found 376.0. |
| F5 | 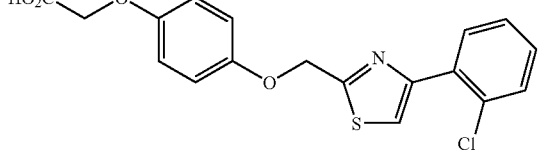 | MS calcd. for C₁₈H₁₅ClNO₄S (M + H⁺) 376.0, found 376.0. |
| F6 | 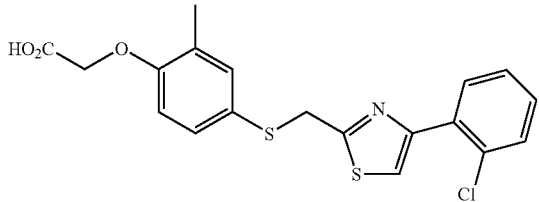 [SMILES: Cc1cc(SCc2nc(-c3ccccc3Cl)cs2)ccc1OCC(=O)O] | MS calcd. for C₁₉H₁₇ClNO₃S₂ (M + H⁺) 406.0, found 406.0. |

TABLE 1-continued

| | Compound Structure | Physical Data<br>$^1$H NMR 400 MHz (DMSO-$d_6$)<br>and/or MS (m/z) |
|---|---|---|
| F7 | 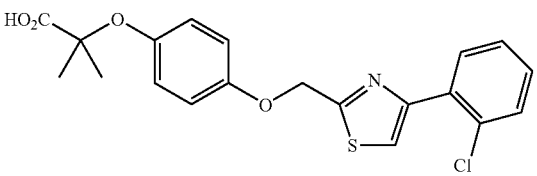 [SMILES: CC(C)(Oc1ccc(OCc2nc(-c3ccccc3Cl)cs2)cc1)C(=O)O] | MS calcd. for $C_{20}H_{19}ClNO_4S$ (M + H$^+$)<br>404.1, found 404.1. |
| F8 | 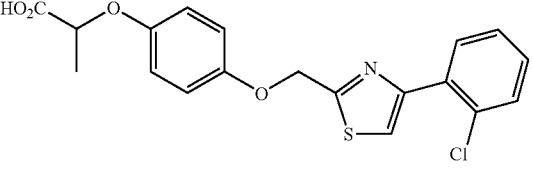 [SMILES: CC(Oc1ccc(OCc2nc(-c3ccccc3Cl)cs2)cc1)C(=O)O] | MS calcd. for $C_{19}H_{17}ClNO_4S$ (M + H$^+$)<br>390.1, found 390.0. |
| F9 | 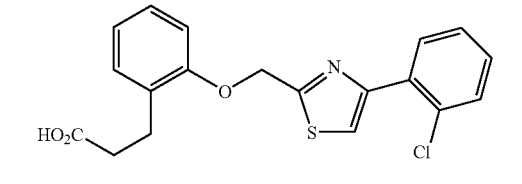 [SMILES: O=C(O)CCc1ccccc1OCc1nc(-c2ccccc2Cl)cs1] | MS calcd. for $C_{19}H_{17}ClNO_3S$ (M + H$^+$)<br>374.1, found 374.1. |
| F10 | 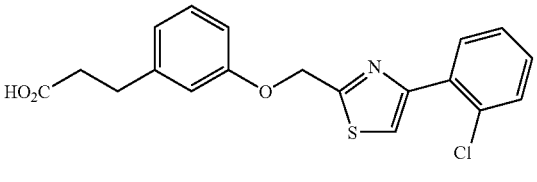 [SMILES: O=C(O)CCc1cccc(OCc2nc(-c3ccccc3Cl)cs2)c1] | MS calcd. for $C_{19}H_{17}ClNO_3S$ (M + H$^+$)<br>374.1, found 374.1. |
| F11 | 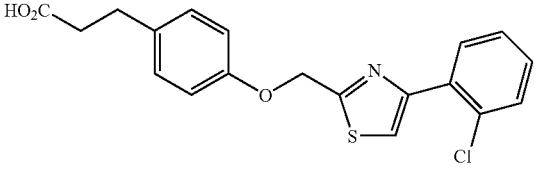 [SMILES: O=C(O)CCc1ccc(OCc2nc(-c3ccccc3Cl)cs2)cc1] | MS calcd. for $C_{19}H_{17}ClNO_3S$ (M + H$^+$)<br>374.1, found 374.1. |
| F12 | 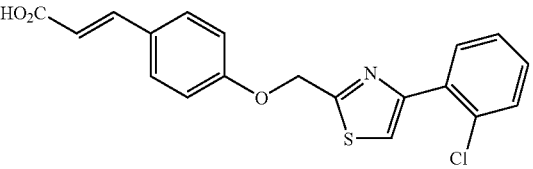 [SMILES: O=C(O)/C=C/c1ccc(OCc2nc(-c3ccccc3Cl)cs2)cc1] | MS calcd. for $C_{19}H_{15}ClNO_3S$ (M + H$^+$)<br>372.0, found 372.0. |
| F13 | 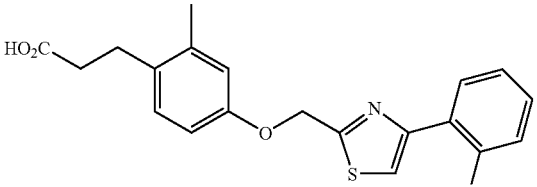 | MS calcd. for $C_{20}H_{19}ClNO_3S$ (M + H$^+$)<br>388.1, found 388.1. |
| F14 | 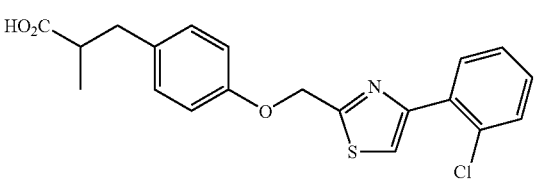 [SMILES: CC(Cc1ccc(OCc2nc(-c3ccccc3Cl)cs2)cc1)C(=O)O] | MS calcd. for $C_{20}H_{19}ClNO_3S$ (M + H$^+$)<br>388.1, found 388.1. |

TABLE 1-continued

| | Compound Structure | Physical Data<br>$^1$H NMR 400 MHz (DMSO-$d_6$)<br>and/or MS (m/z) |
|---|---|---|
| F15 | 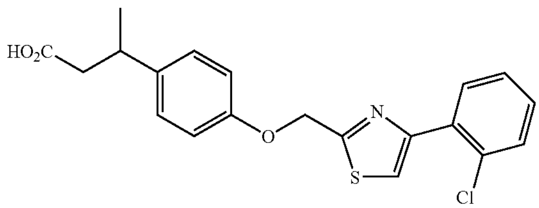 [SMILES: CC(CC(=O)O)c1ccc(OCc2nc(-c3ccccc3Cl)cs2)cc1] | MS calcd. for $C_{20}H_{19}ClNO_3S$ (M + H$^+$)<br>388.1, found 388.1. |
| F16 | 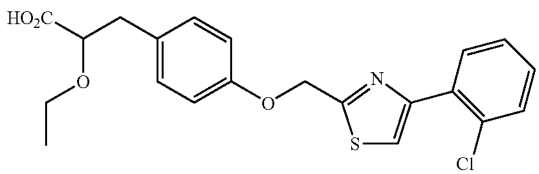 [SMILES: CCOC(Cc1ccc(OCc2nc(-c3ccccc3Cl)cs2)cc1)C(=O)O] | MS calcd. for $C_{21}H_{21}ClNO_4S$ (M + H$^+$)<br>418.1, found 418.1. |
| F17 | 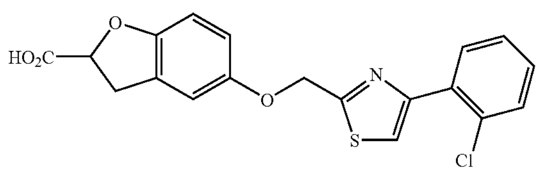 [SMILES: O=C(O)C1Cc2cc(OCc3nc(-c4ccccc4Cl)cs3)ccc2O1] | MS calcd. for $C_{19}H_{15}ClNO_4S$ (M + H$^+$)<br>388.0, found 388.0. |
| F18 | 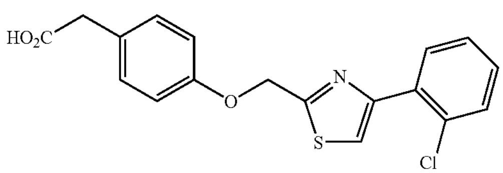 [SMILES: O=C(O)Cc1ccc(OCc2nc(-c3ccccc3Cl)cs2)cc1] | MS calcd. for $C_{18}H_{15}ClNO_3S$ (M + H$^+$)<br>360.0, found 360.0. |
| F19 | 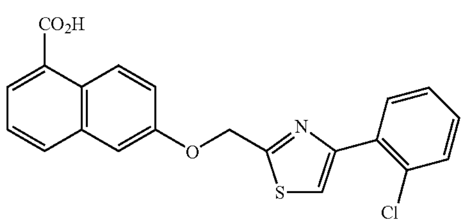 [SMILES: O=C(O)c1cccc2cc(OCc3nc(-c4ccccc4Cl)cs3)ccc12] | MS calcd. for $C_{21}H_{15}ClNO_3S$ (M + H$^+$)<br>396.0, found 396.1. |
| F20 | 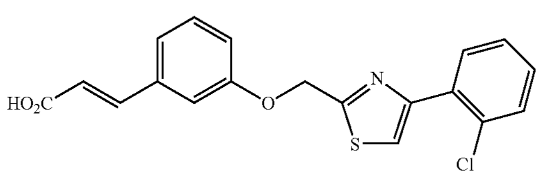 [SMILES: O=C(O)/C=C/c1cccc(OCc2nc(-c3ccccc3Cl)cs2)c1] | MS calcd. for $C_{19}H_{15}ClNO_3S$ (M + H$^+$)<br>372.0, found 372.0. |
| F21 | 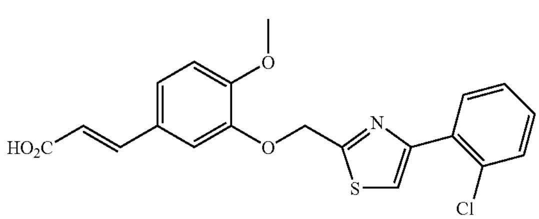 [SMILES: COc1ccc(/C=C/C(=O)O)cc1OCc1nc(-c2ccccc2Cl)cs1] | MS calcd. for $C_{20}H_{17}ClNO_4S$ (M + H$^+$)<br>402.1, found 402.1. |
| F22 | 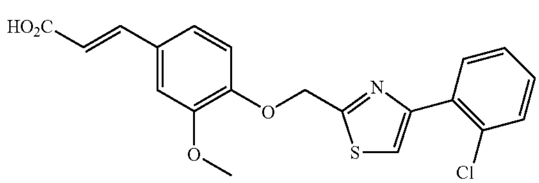 [SMILES: COc1cc(/C=C/C(=O)O)ccc1OCc1nc(-c2ccccc2Cl)cs1] | MS calcd. for $C_{20}H_{17}ClNO_4S$ (M + H$^+$)<br>402.1, found 402.1. |

TABLE 1-continued

| | Compound Structure | Physical Data<br>$^1$H NMR 400 MHz (DMSO-d$_6$)<br>and/or MS (m/z) |
|---|---|---|
| F23 | 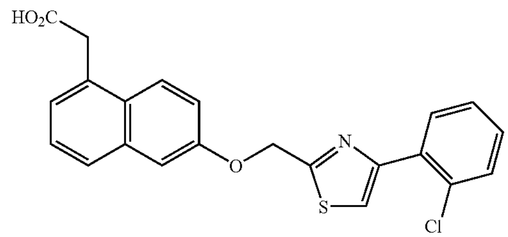 [SMILES: O=C(O)Cc1cccc2cc(OCc3nc(-c4ccccc4Cl)cs3)ccc12] | MS calcd. for $C_{22}H_{17}ClNO_3S$ (M + H$^+$)<br>410.1, found 410.1. |
| F24 | 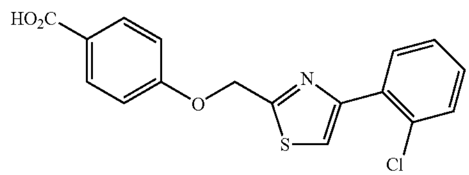 [SMILES: O=C(O)c1ccc(OCc2nc(-c3ccccc3Cl)cs2)cc1] | MS calcd. for $C_{17}H_{13}ClNO_3S$ (M + H$^+$)<br>346.0, found 346.0. |
| G1 | 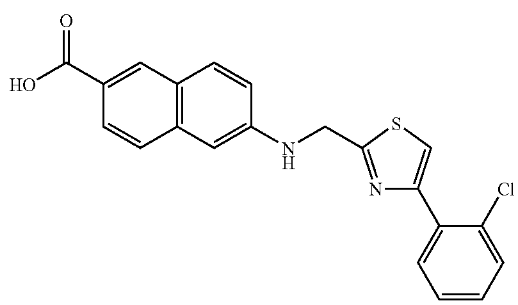 [SMILES: O=C(O)c1ccc2cc(NCc3nc(-c4ccccc4Cl)cs3)ccc2c1] | MS calcd. for $C_{21}H_{16}ClN_2O_2S$ (M + H$^+$)<br>395.9, found 396.0. |
| G2 | 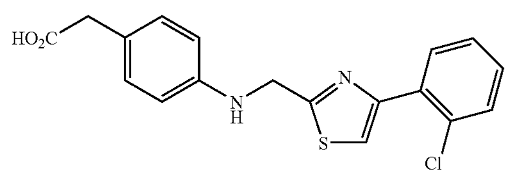 [SMILES: O=C(O)Cc1ccc(NCc2nc(-c3ccccc3Cl)cs2)cc1] | MS calcd. for $C_{18}H_{16}ClN_2O_2S$ (M + H$^+$)<br>359.1, found 359.1. |
| G3 | 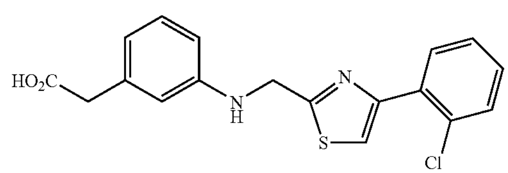 [SMILES: O=C(O)Cc1cccc(NCc2nc(-c3ccccc3Cl)cs2)c1] | MS calcd. for $C_{18}H_{16}ClN_2O_2S$ (M + H$^+$)<br>359.1, found 359.1. |
| G4 | 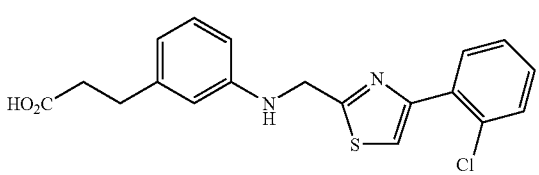 [SMILES: O=C(O)CCc1cccc(NCc2nc(-c3ccccc3Cl)cs2)c1] | MS calcd. for $C_{19}H_{18}ClN_2O_2S$ (M + H$^+$)<br>373.1, found 373.1. |
| G5 | 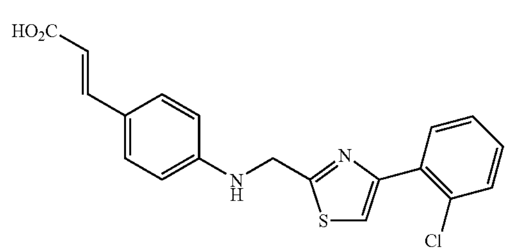 [SMILES: O=C(O)/C=C/c1ccc(NCc2nc(-c3ccccc3Cl)cs2)cc1] | MS calcd. for $C_{19}H_{16}ClN_2O_2S$ (M + H$^+$)<br>371.1, found 371.1. |

TABLE 1-continued

| | Compound Structure | Physical Data<br>$^1$H NMR 400 MHz (DMSO-$d_6$)<br>and/or MS (m/z) |
|---|---|---|
| G6 | 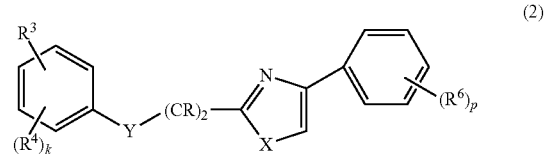 | MS calcd. for $C_{20}H_{18}ClN_2O_2S$ (M + H$^+$)<br>385.1, found 385.1. |
| G7 | 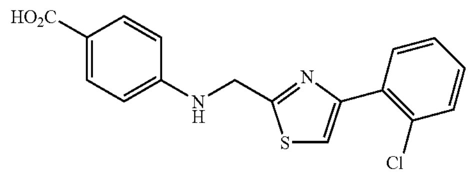 [SMILES: O=C(O)c1ccc(NCc2nc(-c3ccccc3Cl)cs2)cc1] | MS calcd. for $C_{17}H_{14}ClN_2O_2S$ (M + H$^+$)<br>345.0, found 345.0. |

Assays

The suitability of a compound to modulate G protein-coupled receptor 120 (GPR120) may be tested following the assays described below, or using methods known in the art, such as those described in EP 1688138, incorporated herein by reference in its entirety.

Generation of GPR120-Expressing Cells

Human GPR120 stable cell-line was generated in HE 293 cells. GPR120 (Accession number BC101175) is fused to a promiscuous G protein, Gα6. The expression plasmid is transfected into HEK293 cells using Fugene 6 following manufacturer's instruction. Stable cell-lines are generated following drug selection.

FLIPR Assay

FLIPR (Fluorimetric Imaging Plate Reader, Molecular Devices) assays are performed to measure agonist-induced calcium mobilization in the GPR120-expressing cells. One day before the FLIPR assay, HEK293-GPR120-Gα16 cells are seeded into poly-D-lysine coated black-wall-clear bottom 384 well plates (Falcon) at 25,000 cells per well in 40 µl DMEM supplemented with 1% of FBS. The cells are incubated overnight at 37° C. in a humidified incubator. The medium is aspirated on the day of the FLIPR assay. The cells are incubated with 50 µl/well of the assay buffer (HBSS, 20 mM HEPES, 2.5 mM probenecid, pH 7.4) containing Fluo-4 NM dye (Invitrogen cat #F36205) at 37° C. for 45 minutes, and then equilibrated at room temperature for 30 minutes. Compounds are dissolved in DMSO and diluted to desired concentrations with assay buffer. Fluorescent output is measured immediately following compound addition (12.5 µl/well) on the FLIPR machine.

An EC$_{50}$ value was calculated using the change of fluorescent intensity from the reaction initiation. In general, compounds of the invention may have EC$_{50}$ values of 10 µM or less, for example from 0.1 µM to 10 µM. In some examples, compounds of the invention may have EC$_{50}$ values from 0.1 µM to 5 µM; or more particularly from 0.5 µM to 5 µM. In other examples, compounds of the invention may have EC$_{50}$ values of 3 µM or less; for example from 0.1 µM to 3 µM. In yet other examples, compounds may have EC$_{50}$ values less than 0.1 µM or more than 10 µM.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference for all purposes.

The invention claimed is:

1. A compound of Formula (2):

$$\underset{(R^4)_k}{\diagdown}\diagup Y-(CR_2)-\underset{X}{\diagdown}\diagup(R^6)_p \quad (2)$$

or pharmaceutically acceptable salts thereof, wherein:
X is O or S;
Y is NR, O or S;
R$^3$ is —O—(CR$_2$)$_m$—CO$_2$—R, —(CR$_2$)$_m$—CO$_2$—R or —(CH═CH)—CO$_2$—R;
R$^4$ is C$_{1-6}$ alkyl or C$_{1-6}$ alkoxy;
R$^6$ is halo;
each R is H or C$_{1-6}$ alkyl;
k is 1;
m is 0-3; and
p is 1-2.

2. The compound of claim 1, wherein R$^6$ is chloro.

3. The compound of claim 1, wherein said compound is selected from the group consisting of:

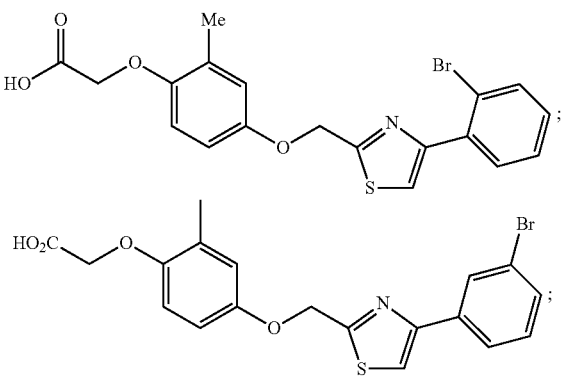

-continued
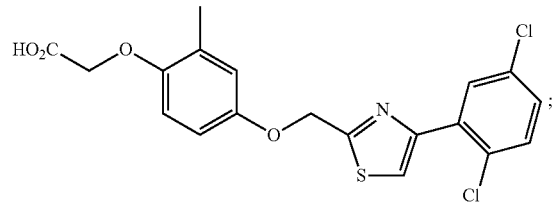
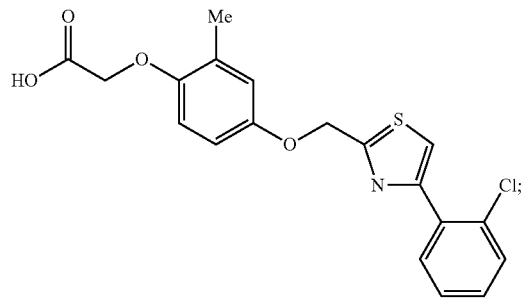
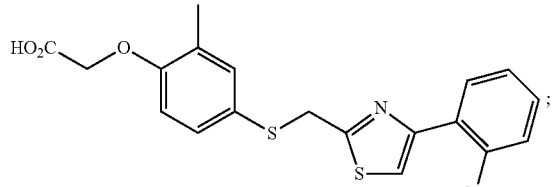
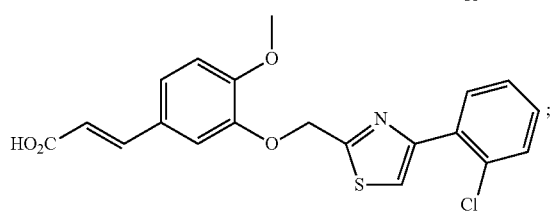
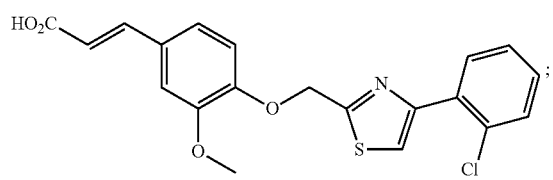
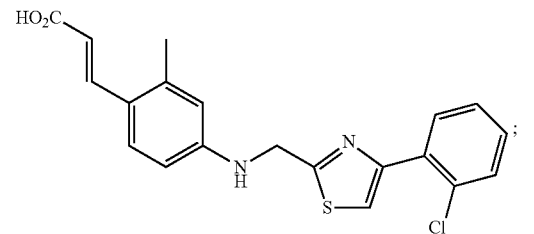
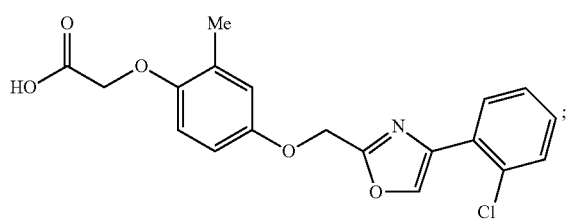
or a pharmaceutically acceptable salt thereof.
4. A pharmaceutical composition comprising a therapeutically effective amount of a compound according to claim 1.
5. A compound selected from the group consisting of:
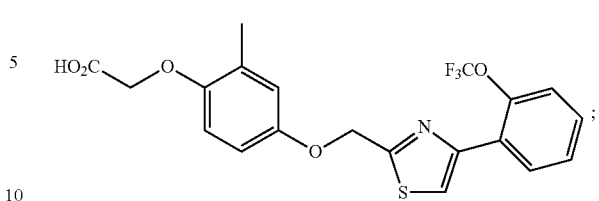
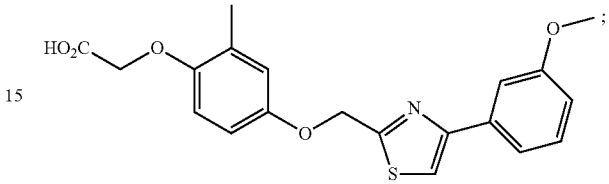
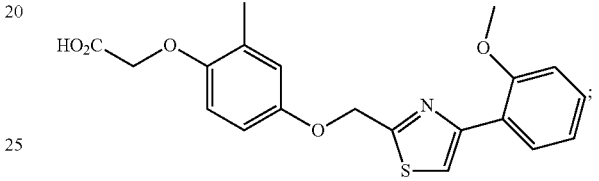
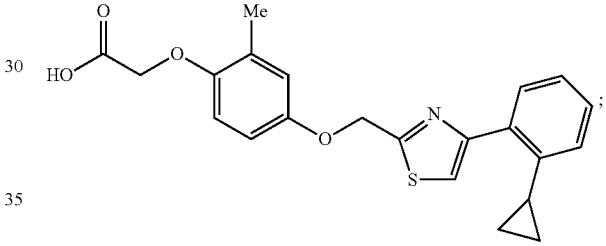
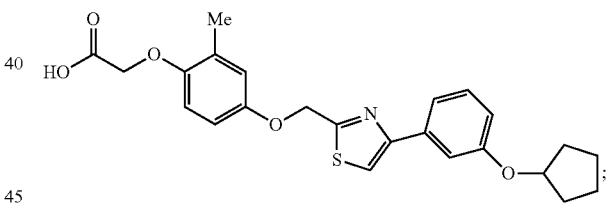
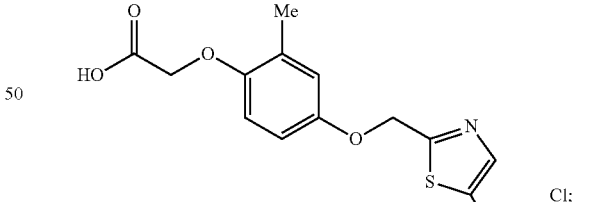
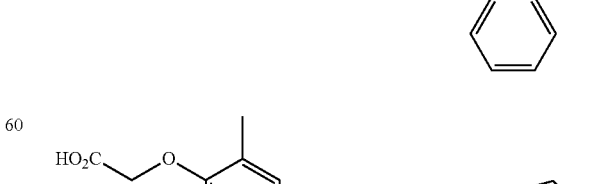
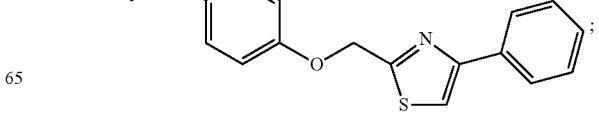

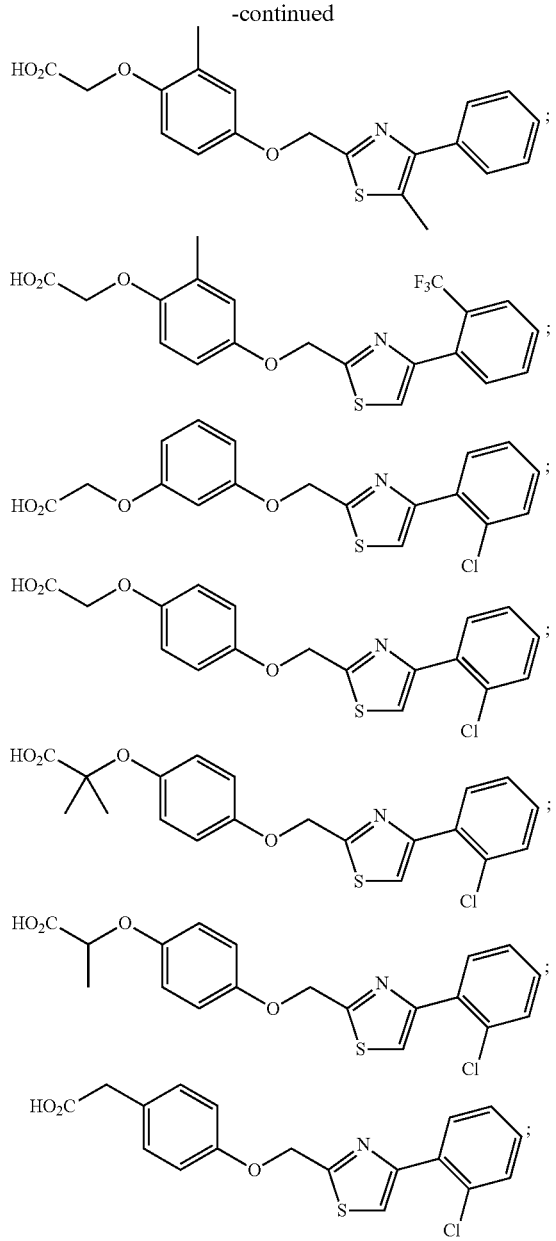
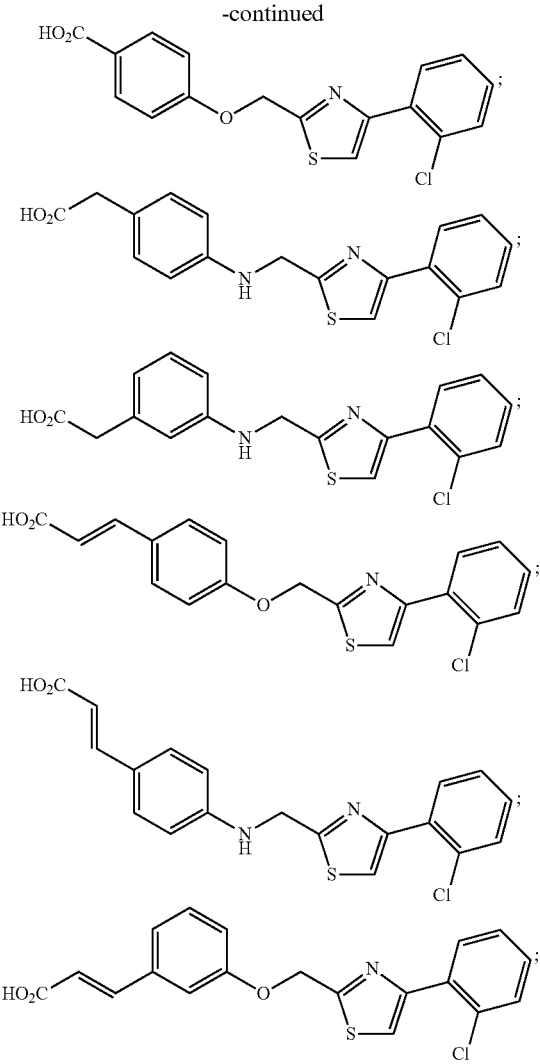
or a pharmaceutically acceptable salt thereof.
6. A pharmaceutical composition comprising a therapeutically effective amount of a compound according to claim 5.
* * * * *